US012383677B2

(12) United States Patent
Plumptre et al.

(10) Patent No.: US 12,383,677 B2
(45) Date of Patent: Aug. 12, 2025

(54) SYSTEM FOR A DRUG DELIVERY DEVICE

(71) Applicant: Sanofi, Paris (FR)

(72) Inventors: David Aubrey Plumptre, Warwick (GB); Hugh Smith, Warwick (GB)

(73) Assignee: Sanofi, Paris (FR)

( * ) Notice: Subject to any disclaimer, the term of this patent is extended or adjusted under 35 U.S.C. 154(b) by 1138 days.

(21) Appl. No.: 17/259,607

(22) PCT Filed: Jul. 15, 2019

(86) PCT No.: PCT/EP2019/068971
§ 371 (c)(1),
(2) Date: Jan. 12, 2021

(87) PCT Pub. No.: WO2020/016162
PCT Pub. Date: Jan. 23, 2020

(65) Prior Publication Data
US 2021/0316076 A1    Oct. 14, 2021

(30) Foreign Application Priority Data

Jul. 18, 2018   (EP) .................................... 18305977

(51) Int. Cl.
*A61M 5/24*          (2006.01)
(52) U.S. Cl.
CPC ....... *A61M 5/24* (2013.01); *A61M 2005/2403* (2013.01)
(58) Field of Classification Search
CPC ............ A61M 5/24; A61M 2005/2403; A61M 2005/2437; A61M 2005/2488;
(Continued)

(56) References Cited

U.S. PATENT DOCUMENTS

| | | | |
|---|---|---|---|
| 2013/0131604 A1* | 5/2013 | Avery .................. | A61B 8/4416 604/207 |
| 2014/0012208 A1* | 1/2014 | Plumptre .......... | A61M 5/31528 604/207 |

FOREIGN PATENT DOCUMENTS

| | | |
|---|---|---|
| CN | 102917739 | 2/2013 |
| EP | 1423079 | 7/2006 |

(Continued)

OTHER PUBLICATIONS

PCT International Search Report and Written Opinion in International Application No. PCT/EP2019/068971, dated Aug. 20, 2019, 10 pages.

(Continued)

*Primary Examiner* — Lauren P Farrar
(74) *Attorney, Agent, or Firm* — Fish & Richardson P.C.

(57) ABSTRACT

A system for a drug delivery device is provided. The system includes: a housing and a cartridge unit that is attachable to the housing or releasably attached to the housing. The cartridge unit includes a cartridge unit guide feature, the cartridge unit guide feature being provided to establish a guiding interface with the housing in order to guide relative movement of the cartridge unit and the housing with respect to one another when attaching the cartridge unit to the housing. The cartridge unit includes a cartridge unit interface feature, the cartridge unit interface feature being provided to form a further interface, in addition to the guiding interface, with the housing of the further interface being established when the cartridge unit is attached to the housing. The guiding interface is a bayonet-type interface which defines at least two different stages of movement between the cartridge unit and the housing when the cartridge unit is attached to the housing, a first stage with at least axial movement by a first stage axial distance in a first stage axial direction and a second stage with at least rotational move- (Continued)

ment by a second stage angle in a second stage rotational direction. The further interface is or includes a ramp interface.

18 Claims, 15 Drawing Sheets

(58) Field of Classification Search
CPC .... A61M 2205/582; A61M 2205/6045; A61M 5/31566
See application file for complete search history.

(56) References Cited

FOREIGN PATENT DOCUMENTS

| | | |
|---|---|---|
| EP | 2043708 | 12/2010 |
| EP | 2555462 | 2/2013 |
| JP | 2013-524909 | 6/2013 |
| JP | 2013-529405 | 7/2013 |
| JP | 2013-534831 | 9/2013 |
| JP | 2014-513600 | 6/2014 |
| JP | 2017-530803 A | 10/2017 |
| WO | WO 2008/059063 | 5/2008 |
| WO | WO 2011/032883 | 3/2011 |
| WO | WO 2011/089206 | 7/2011 |
| WO | WO 2011/089207 | 7/2011 |
| WO | WO 2011/124631 | 10/2011 |
| WO | WO 2011/131775 | 10/2011 |
| WO | WO 2011/131777 | 10/2011 |
| WO | WO 2011/131779 | 10/2011 |
| WO | WO 2011/131783 | 10/2011 |
| WO | WO 2012/064258 | 5/2012 |
| WO | WO 2012/130704 | 10/2012 |
| WO | WO 2016/055636 | 4/2016 |
| WO | WO 2016/065220 | 4/2016 |
| WO | WO 2016/091554 | 6/2016 |
| WO | WO 2016/150900 | 9/2016 |
| WO | WO 2017/186435 | 11/2017 |

OTHER PUBLICATIONS

PCT International Preliminary Report on Patentability in International Application No. PCT/EP2019/068971, dated Jan. 19, 2021, 8 pages.

* cited by examiner

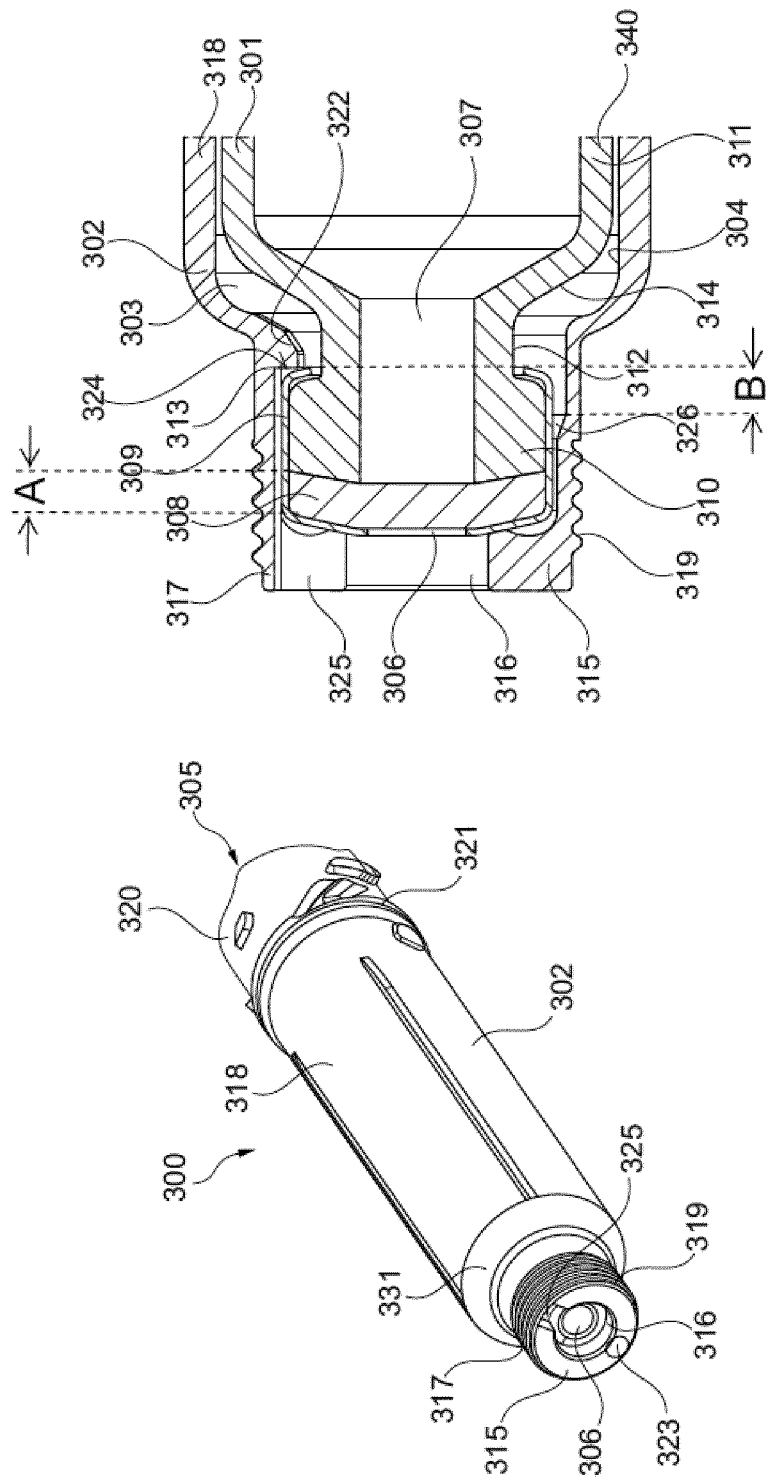

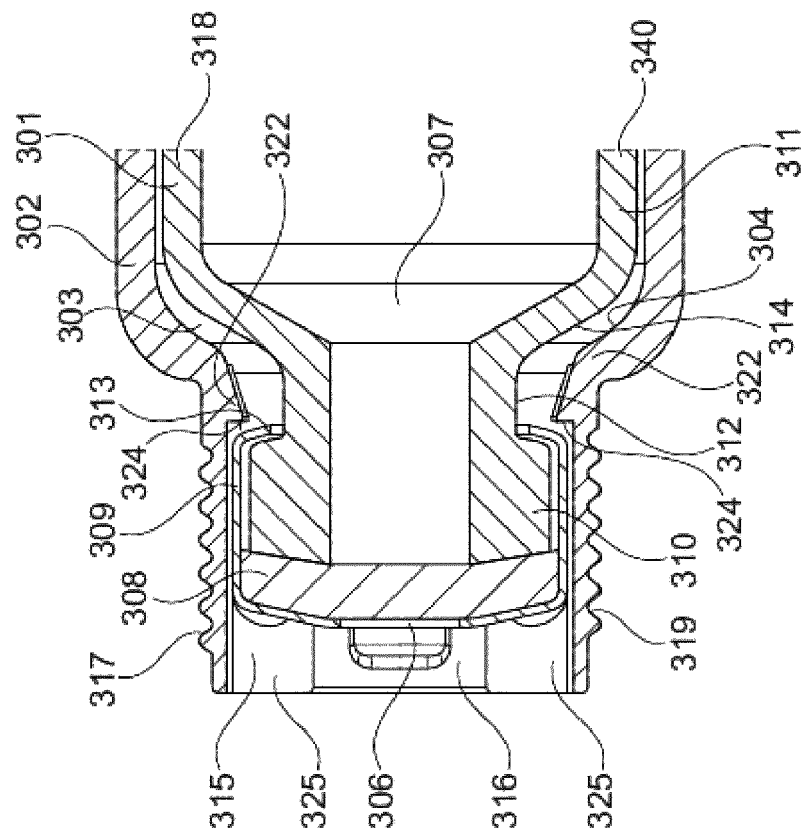
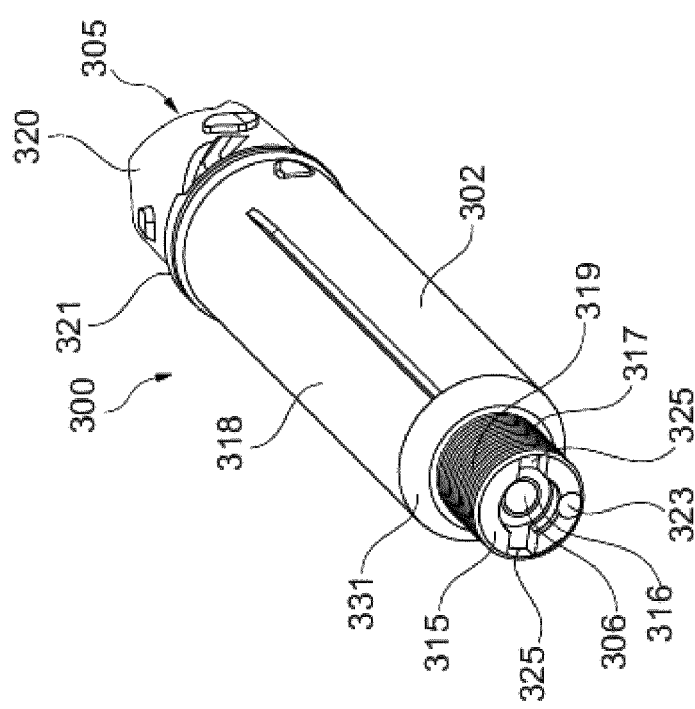
Fig. 2B
Fig. 2A

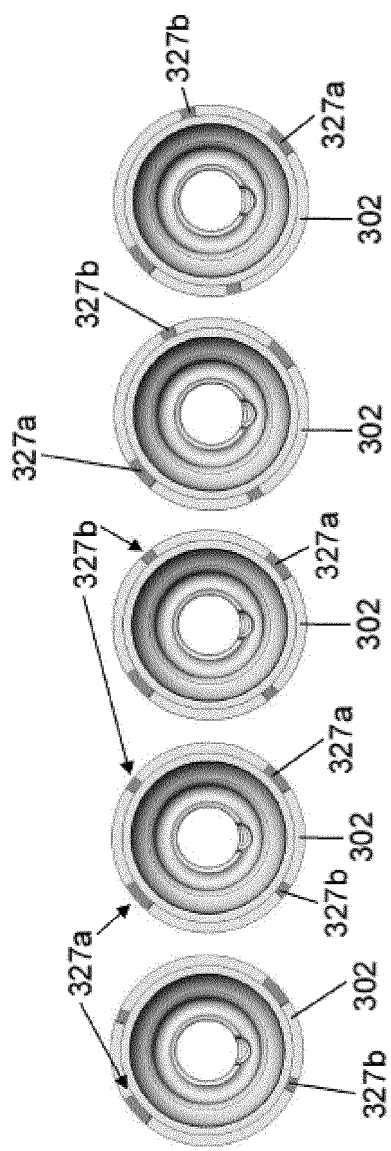
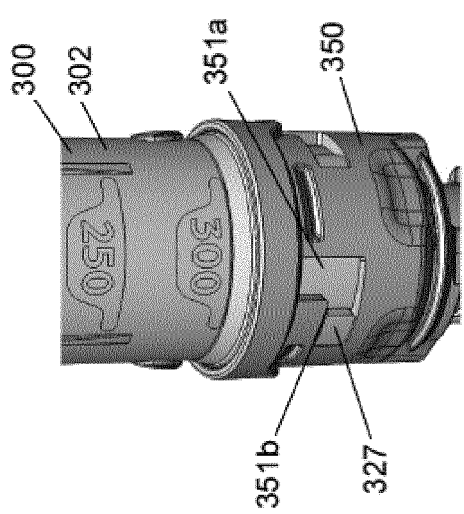
Fig. 11
Fig. 10

SYSTEM FOR A DRUG DELIVERY DEVICE

CROSS REFERENCE TO RELATED APPLICATIONS

The present application is the national stage entry of International Patent Application No. PCT/EP2019/068971, filed on Jul. 15, 2019, and claims priority to Application No. EP 18305977.3, filed on Jul. 18, 2018, the disclosures of which are incorporated herein by reference.

TECHNICAL FIELD

This disclosure relates to a system for a drug delivery device, preferably an injection device and/or a pen-type device, such as a pen-type injector.

BACKGROUND

In regular drug delivery devices, where a single drive mechanism which may be housed in a housing of the drug delivery device is used in conjunction with several cartridges or ampules to dispense drug contained in the cartridge or ampule from the device, usually a cartridge holder of the device is releasably connected or attached to the housing and can be removed or detached from the housing to replace a used cartridge. For doing so, the cartridge holder is disconnected from the housing, the used cartridge is removed from the holder and replaced with a new cartridge which is inserted into the cartridge holder, where the cartridge holder is again attached to the housing and the device is ready to be used again to dispense drug from the new cartridge.

Devices of this kind, however, do have several risks. For example, a cartridge containing a drug for which the mechanism of the drug delivery device is not specifically designed, i.e. a wrong drug, can be inserted into the cartridge holder and the user does not realize that he has put the wrong drug cartridge into the cartridge holder. This mistake may be lethal for the user and is also likely to occur as cartridges with different drugs usually look pretty much alike. Furthermore, the cartridge, if sold as a separate item, is usually easily damaged, in particular as the standard cartridges are usually glass cartridges.

SUMMARY

It is an object of the present disclosure to provide improvements related to drug delivery devices. This object and potentially other objects are solved by the present disclosure and, particularly, by the subject-matter of the independent claim. Advantageous embodiments and refinements are subject to the dependent claims.

One aspect of the present disclosure relates to a system for a drug delivery device. Another aspect relates to a drug delivery device which comprises the system. The drug delivery device preferably comprises a medicament. Still another aspect relates to an arrangement which comprises the system or the device.

In an embodiment, the system comprises a housing. The housing may house one or more components of a dose setting and/or drive mechanism such as a piston rod and/or a dose setting member which is movable relative to the housing for setting a dose and/or for delivering the set dose, for example. The piston rod may be moved in the distal direction relative to the housing during dose delivery, expediently by a distance which corresponds to the size of the dose which has been set previously by the dose setting member.

The system furthermore comprises a cartridge unit. The cartridge unit is attachable to the housing or, preferably releasably, attached to the housing. If it is releasably attached, the cartridge unit may be attached to the housing and, after having been attached, be detached. The cartridge unit may comprise or retain a drug or medicament which is to be delivered from the drug delivery device. When the cartridge unit is attached to the housing, the system may form the drug delivery device. The cartridge unit furthermore comprises a cartridge unit guide feature. The cartridge unit guide feature is expediently provided to establish a guiding interface with the housing, such as by cooperating with a housing guide feature provided in or on the housing, in order to guide relative movement of the cartridge unit and the housing with respect to one another, e.g. when attaching the cartridge unit to the housing or when detaching the cartridge unit from the housing. The cartridge unit may comprise one or a plurality of cartridge unit guide features. The housing may comprise one or more housing guide features. The respective housing guide feature may be arranged to cooperate with one cartridge unit guide feature. The cartridge unit further comprises a cartridge unit interface feature. The cartridge unit interface feature may be provided to form a further interface, e.g. in addition to the guiding interface, with the housing. The cartridge unit interface feature(s) may be different from the cartridge unit guide feature(s). The cartridge unit guide feature(s) and the cartridge unit interface feature(s) may be axially and/or angularly offset from one another. The cartridge unit may comprise one or more than one cartridge unit interface features. The housing may comprise one or more housing interface features. The housing interface feature(s) may interact with the cartridge unit interface feature(s) to form the further interface. The further interface may be established during the attachment of the cartridge unit to the housing. The further interface is expediently established when the cartridge unit is attached to the housing. The further interface may be established while the relative movement is guided by the guiding interface. Thus, when the cartridge unit is attached to the housing, the guiding interface may already be established and guide the relative movement before the further interface is established.

In an embodiment, the guiding interface defines at least two different stages of movement between the cartridge unit and the housing when the cartridge unit is attached to the housing, a first stage and a second stage. When the cartridge unit is attached to the housing, the first stage may precede the second stage. When the cartridge unit is detached, the second stage may precede the first stage. The first stage may be a stage with at least axial movement, such as only axial movement or axial and rotational movement, i.e. helical movement, of the cartridge unit with respect to the housing. The cartridge unit may be moved during the first stage by a first stage axial distance in a first stage axial direction. The first stage axial direction may be a direction towards the housing. In the second stage the relative movement of the cartridge unit with respect to the housing comprises at least rotational movement by a second stage angle in a second stage rotational direction. The second stage may comprise only rotational movement or rotational and axial, e.g. helical, movement. The helix along which the helical movement in the second stage takes place and the helix along which the helical movement in the first stage takes place may be oppositely handed. In the first stage, the movement of the cartridge unit relative to the housing may be predominantly axially. That is to say the axial distance which is covered during this movement may be greater than the angular distance by which the cartridge unit guide feature is rotated. In the second stage, if this stage comprises rotational and axial movement, the movement may be predominantly rotational. Consequently, the angular distance traveled by the cartridge unit guide feature may be greater than the axial distance. The first stage axial distance may be greater than the second stage axial distance. The second stage angular distance may be greater than the first stage angular distance. The axis along which the cartridge unit is moved or around which it is rotated may be a main longitudinal axis of the housing and/or the cartridge unit. The guiding interface may be a bayonet or bayonet-type interface.

In an embodiment, the system is configured such that the cartridge unit is moved relative to the housing in the second stage by a second stage axial distance in a second stage axial direction when the cartridge unit is attached to the housing. The second stage axial direction may be opposite to the first stage axial direction. Thus, the cartridge unit may be moved away from the housing during the second stage, e.g. helically. The second stage axial distance may be less than the first stage axial distance. The axial movement during the second stage may have several advantages. Firstly, the movement in the opposite axial direction during the second stage may occur right before the end of the attachment procedure of the cartridge unit to the housing. Accordingly, as this movement is notable for the user, the user may gain confidence that he has attached the cartridge unit correctly. Furthermore, the axial movement in the opposite axial direction may assist in providing a defined initial position for the drug delivery such that already the first dose of drug which is dispensed from the device can be dispensed accurately and a priming operation can be avoided. Still further, the movement in the opposite axial direction may be used to reestablish an operational connection between two or more elements of the dose setting and/or drive mechanism of the drug delivery device. Such a connection may be required to deliver already the first dose accurately.

In an embodiment, the further interface is a ramp interface or comprises a ramp interface. Ramp interfaces have several advantages as is detailed below.

In an embodiment, the further interface is established after the first stage has been completed, e.g. during or at the beginning of the second stage.

In an embodiment, the housing interface feature and/or the cartridge unit interface feature comprise a ramp surface. That is to say, the respective interface feature may be a ramp feature. The ramp surface may extend angularly, preferably predominantly angularly. The ramp surface may face in the distal direction, e.g. when provided on the housing. The ramp surface may face in the proximal direction, e.g. when provided on the cartridge unit. The distally facing ramp surface may rise in the second stage rotational direction. The proximally facing ramp surface may rise in the direction opposite the second stage rotational direction.

In an embodiment, the movement by the second stage axial distance is defined or governed by the ramp interface. That is to say, the ramp interface may be established during the second stage. The slope of the ramp surface which is contacted by the interface feature, either the housing or the cartridge unit interface feature, in combination with the second stage rotation angle may be adjusted such that the cartridge unit is moved by the second stage axial distance away from the housing.

In an embodiment, the ramp surface is part of a ramp structure which comprises a plurality of ramp surfaces, which are preferably axially aligned and/or all rise in the same rotational direction. The ramp surfaces may be arranged in a pattern which is rotationally symmetric. The ramp surfaces may be circumferentially disposed around the main longitudinal axis of the housing or the cartridge unit respectively.

In an embodiment, a slope or a pitch of the ramp surface is less than or equal to a slope or a pitch of the helical movement during the second stage, which may correspond to the helix angle of the helix which corresponds to the helical movement, and/or a slope or pitch defined by the second stage axial distance and the second stage angle. If the slope of the ramp surface is equal to the slope during the second stage, the ramp surface may be used to generate the axial movement in the second stage axial direction. If the slope of the ramp surface is less than the slope during the second stage, the ramp surface does not hinder the movement in the second stage axial direction. In the latter case, the movement in the second stage axial direction may be generated by the guiding interface, for example. However, a ramp structure comprising the ramp surface may still be used for coding purposes as is discussed further below.

In an embodiment, the angular extension of the ramp surface is greater than or equal to the angular extension defined by the second stage angle, such as the angular extension defined by the second stage angle at the radial position of the ramp surface. In this way, the ramp surface may be adjusted to drive the axial movement during the second stage.

In an embodiment, the height difference between opposite ends of the ramp surface, in particular between opposite angular ends which delimit the ramp surface angularly, is greater than or equal to the second stage axial distance.

In an embodiment, the ramp interface is not established until after the first stage of movement has been completed when the cartridge unit is attached to the housing.

In an embodiment, the respective ramp surface has a constant slope in the angular or rotational direction.

In an embodiment, the cartridge unit comprises at least one cartridge unit coding structure. The cartridge unit coding structure may be formed by means of one or more cartridge unit coding features.

In an embodiment, the housing comprises at least one housing coding structure. The housing coding structure may be formed by means of one or more housing coding features.

The cartridge unit coding structure may be provided to establish a coding interface with the housing coding structure of the housing. The coding interface may be established before the second stage of movement, e.g. during the first stage or even preceding the first stage. By means of the coding interface it can be ensured that the housing and/or the drive mechanism retained in the housing match the drug, drug formulation, filling volume and/or dimension of a cartridge or drug contained in the cartridge unit. If the cartridge unit coding structure and the housing coding structure do not match, attachment of the cartridge unit to the housing is prevented. For this purpose, the coding features may cooperate mechanically and block further movement of the cartridge unit relative to the housing. The coding ensures that only matching pairs of housings and cartridge units can be connected. Consequently, it can be avoided that wrong drugs or drug formulations or cartridges of the wrong dimensions are coupled to a specific mechanism. The respective cartridge unit coding feature may be axially and/or angularly separated from the cartridge unit interface feature, e.g. distally or proximally. Thus, the coding interface and the further interface may be separate interfaces. Alternatively or additionally, the coding interface and the guiding interface may be separate interfaces. Thus, standard guiding and/or further interfaces may be used whereas a differentiation between different cartridge units such as with respect to the drug, the drug formulation and/or the dimension of cartridge retained in the cartridge unit can be achieved via specifically designed coding features. For example, the coding features may be axially aligned, where the angular width and/or the angular pitch and/or the number of coding features can be varied to code different cartridge units to different housings retaining different drive mechanisms. The coding interface is particularly different from the ramp interface. If applicable, the guide features can be used for coding purposes, e.g. by varying the angular width and/or distribution of the guide features.

In an embodiment, the coding feature is provided in addition to the cartridge unit guide feature and/or the ramp feature(s).

In an embodiment, the respective housing coding feature may be axially separated from the housing interface feature or from all housing interface features. In particular, the coding feature may be axially separated from the features involved in the ramp interface.

In an embodiment, the cartridge unit coding feature is an axially extending feature. The axially extending feature may be delimited in an angular direction, preferably in the direction opposite to the second stage rotational direction, by a surface, i.e. an angular surface, which has a length or an axial extension which is greater than or equal to the first stage axial distance. In this way, it is ensured that an axial travel of the cartridge unit relative to the housing by the first stage axial distance is allowed, where the surface may travel along a surface of a housing coding feature which faces the surface of the cartridge unit coding feature. The surface of the housing coding feature may be an angularly facing or angular surface, which delimits the housing coding feature in the angular direction. This is the case, if the coding structures of the housing and the cartridge unit match and, consequently, the cartridge unit can be attached to the housing. During the second stage, the angularly facing surfaces may be separated by an angular distance defined by the second stage angle. When the cartridge unit has been connected to the housing, the angularly facing surfaces of the housing coding feature and the one of the cartridge coding feature may still face one another. If the coding structures of the housing and the cartridge unit do not match, the cartridge unit coding feature, e.g. a proximally facing surface thereof, may abut the housing coding feature, e.g. a distally facing surface thereof. This abutment may block further axial movement of the cartridge unit towards the housing, particularly during the first stage. The distally facing surface of the housing coding feature may be arranged close to the angular surface of the housing coding feature. Thus, during or before the first stage of movement, non-matching coding structures may prevent further axial movement due to abutment of the cartridge unit coding feature and the housing coding feature, in particular axially facing surfaces thereof.

In an embodiment, the respective housing coding feature is an axially extending feature. The respective housing coding feature may be delimited in an angular direction, preferably in the rotational direction in the second stage, by an angular surface which may have an axial extension, in particular along the ramp surface, which is less than or equal to the first stage axial distance. In this way, it may be ensured that a ramp surface can be reached by a cartridge unit interface feature to establish the ramp interface after the axial movement during the first stage has been completed.

In an embodiment, the ramp surface is adjoined angularly, e.g. in a direction opposite to the second stage rotational direction, by an angular surface which extends along the ramp surface axially. In this way, it can be achieved that once the cartridge unit has traveled by the first stage axial distance, the ramp interface is established such that, during the second stage of movement, the cartridge unit is displaced distally by the second stage axial distance relative to the housing.

In an embodiment, the housing coding feature and the ramp surface and/or the cartridge unit coding feature are integrated in a common ramp structure. Specifically, a surface region which delimits a ramp surface of the ramp structure, e.g. in the second stage rotational direction or the opposite rotational or angular direction, may be provided as a coding surface which is abutted by the cartridge unit coding feature of a non-matching cartridge unit during the first stage. If the cartridge unit is a matching cartridge unit with a matching coding structure, the cartridge unit coding feature pass the ramp surface and the cartridge unit interaction feature or the ramp surface of the cartridge unit may cooperate with the ramp surface during the second stage.

In an embodiment, the respective housing coding feature and/or the respective cartridge unit coding feature is formed by a feature which is part of the same ramp structure as the ramp surface but angularly offset from the ramp surface, e.g. in a direction opposite to the second stage rotational direction or in the second stage rotational direction. The respective coding feature may be a, preferably axially oriented, protrusion.

In an embodiment, the cartridge unit comprises a cartridge holder and/or a cartridge. The cartridge may be received or arranged in the cartridge holder. The cartridge may contain a drug or drug formulation or a medicament. A proximal end of the cartridge may be closed by a movable bung or piston. Provided that fluid communication between the interior of the cartridge and the exterior is established such as by a needle piercing a septum at the distal end of the cartridge, and the bung is displaced in the distal direction with respect to the cartridge towards an outlet of the cartridge, the content of the cartridge may be dispensed from the cartridge. The cartridge unit guide feature may be provided on an exterior surface of the cartridge holder, e.g. a side wall of the cartridge holder. The cartridge unit guide feature may be provided in a proximal section of the cartridge holder. The proximal section may be received in the housing when the cartridge holder and the housing have been connected.

In an embodiment, the cartridge unit is a cartridge assembly. The assembly may comprise the cartridge and the cartridge holder. The cartridge may be permanently and/or irreleasably secured in the cartridge holder. Thus, the cartridge unit may form a disposable item. Alternatively, the cartridge may be releasably secured in the cartridge holder. The cartridge holder may be that part of the cartridge unit which is provided with the guide feature, the interface feature and/or the coding feature. Thus, a standard cartridge design need not be changed for coding, guiding, and/or interface purposes. The cartridge holder may provide additional protection for the cartridge. Further, standard cartridges, e.g. of 1.5 mL or 3.0 mL volumes, may be used, e.g. for different drugs or drug formulations. The cartridge assemblies may be assembled by the manufacturer and distributed. The adjustments to the different housings, drive mechanisms, interfaces and/or codings may be effected by using different cartridge holders.

In an embodiment, the cartridge unit interface feature(s) and/or the cartridge unit coding feature(s) is(are) axially offset from the cartridge unit guide feature(s). The cartridge unit interface feature(s) and/or the cartridge unit coding feature(s) may be proximally or distally offset from the cartridge unit guide feature(s). The cartridge unit interface feature(s) and/or the cartridge unit coding feature(s) may be integrated into the proximal rim or end wall of the cartridge holder. In this case, there will be a proximal offset.

In an embodiment, the cartridge holder comprises a protruding portion on its exterior. The protruding portion may extend circumferentially around the cartridge holder, e.g. flange-like. The cartridge unit interface feature(s) and/or the cartridge unit coding feature(s) may be provided on the protruding portion, e.g. on a proximal surface thereof. The cartridge unit guide feature(s) may be arranged proximally relative to the protruding portion.

In an embodiment, the guiding interface is a standard interface. Accordingly, in different cartridge units, the guide features may be formed alike. Differences may be present in the interface features and/or the coding features. Thus, the general connection or guiding mechanisms may operate alike in all of the drug delivery devices of a set of devices, the housing of each device being connectable only to the cartridge unit with the matching coding structure or coding features. In the set or the arrangement the matching coding structures of pairs of housings and cartridge units may be unique.

In an embodiment, an arrangement comprises the system as disclosed above. The cartridge unit of the system may be a first cartridge unit and the arrangement may comprise a second cartridge unit. The second cartridge unit may be configured in the same way as the first cartridge unit. In particular it may have cartridge unit guide feature(s) and/or cartridge unit interface feature(s), preferably of the same configuration and relative arrangement. Expediently, the coding structures of the first and second cartridge units are different. This is particularly expedient, if the second cartridge unit and the first cartridge unit contain different drugs or drug formulations and/or comprise cartridges of different dimensions. Cartridges of different dimensions may comprise cartridges of different lengths and/or diameters such as inner or outer diameter.

In the present context "different drugs" may mean that the cartridge units contain drugs based on different active pharmaceutical ingredients. "Different drug formulations" may mean that the formulations may be based on the same active pharmaceutical ingredient but the cartridge units comprise liquid with different concentrations of the active pharmaceutical ingredient, for example.

The first cartridge unit guide feature and the second cartridge unit guide feature may be arranged and configured alike and/or the cartridge unit coding structures of the first and second cartridge unit may be different. The cartridge unit coding structure of the first cartridge unit and the housing coding structure of the housing match one another or are compatible with one another. Thus, the first cartridge unit can be attached to the housing. The cartridge unit coding structure of the second cartridge unit and the housing coding structure expediently do not match one another such that the second cartridge unit cannot be attached to the housing. Thus, although the guide features of the second cartridge unit and of the housing would potentially be compatible with one another, the non-matching coding structures prevent that the second cartridge unit can be attached to the (first) housing. The second cartridge unit may have a coding structure which is matched to a second housing, where the coding structure of the first cartridge unit prevents attachment of the first cartridge unit to the second housing. However, the first and second cartridge unit, when connected to the first housing or the second housing respectively may perform the same sequence of movements, preferably, by the same angular and/or axial distances. Thus, although the cartridge units are different, the attachment sequence of movements may be familiar to the user already as may be the pattern of the guide features and/or their dimensions.

Preferably, the second cartridge unit can be attached to the second housing and the first cartridge unit cannot on account of the different cartridge unit coding structures. Just like the first housing and the first cartridge unit, the second cartridge unit and the second housing may have cartridge unit interface features and housing interface features which cooperate to form a further interface, in addition to a guiding interface, during the attachment. The further interface comprises a ramp interface. A first ramp surface which governs, defines or participates in the ramp interface between the first housing and the first cartridge unit and a second ramp surface which governs, defines or participates in the ramp interface between the second housing and the second cartridge unit may have the same slope. The angular extension of the respective ramp surface may be greater than or equal to the angular extension defined by the rotation by the second stage rotation angle.

In other words, the first cartridge unit and the second cartridge unit and/or the first housing and the second housing may comprise ramp surfaces of the same slope and/or of an angular extension which is at least as great as the one defined by the second stage rotation angle. Thus, by providing the ramp structure with integrated ramp surface(s) and coding feature(s), a coding geometry or coding system is employed which can be established in drug delivery devices without having to adjust many parts or molds for the parts.

In an embodiment the cartridge unit and/or housing guide features may be used for coding purposes, e.g. by varying the widths and angular positions between guide features for the first cartridge unit and housing and guide features for the second cartridge unit and housing. Ramp surfaces of the same slope may nevertheless be provided in the first and second housing and/or in the first and second cartridge unit. However the respective ramp structure does not include the coding features.

In other words, the first ramp surface may be part of a first ramp structure which comprises a plurality of ramp surfaces and the second ramp surface may be part of a second ramp structure which comprises a plurality of ramp surfaces, wherein the first ramp structure and the second ramp structure are configured alike or in the same way.

In an embodiment, a first coding feature—housing or cartridge unit coding feature of the first housing or first cartridge unit—is axially offset from the first ramp structure and a second coding feature—housing or cartridge unit coding feature of the second housing or second cartridge unit—is axially offset from the second ramp structure.

In an embodiment, the ramp structures of the two cartridge units are configured alike but the angular pitch of the cartridge unit coding feature and/or the angular width of the cartridge unit coding features varies between the first and second cartridge unit. In this way, it can be prevented that the second cartridge unit can be attached to the housing. In this case, one or more of the cartridge unit or housing guide features may form the cartridge unit or housing coding features.

In an embodiment, the cartridge unit coding feature of both cartridge units may be delimited in the angular direction by a surface which has a length which is greater than or equal to the first stage axial distance.

In an embodiment of a set or arrangement with two drug delivery devices, where the drug delivery devices comprise different drugs or drug formulations in the cartridge units and/or cartridges with different dimensions, the cartridge unit of the first device expediently cannot be attached to the housing of the second device and, preferably, vice versa. Thus, crosswise connection of cartridge units to different drive mechanisms which are retained in housings having the same general outer appearance may be avoided by way of the different cartridge unit coding structures of the respective cartridge unit which are not compatible with the housing coding structure of the other drug delivery device. Both devices may have corresponding ramp interfaces which may be established and/or act during the second stage of movement.

In an embodiment of a set of or an arrangement with two different drug delivery devices, each of the devices being one as explained above, the cartridge units of any one the devices can be disconnected from the housing of the device and connected to the housing of the other drug delivery device. These two cartridge units expediently comprise the same drug or drug formulation and/or cartridges of the same dimensions, e.g. length, diameter, and/or volume. The two devices preferably also comprise identical, e.g. shaped and/or arranged, cartridge unit interface features and/or housing interface features, and/or cartridge unit coding features and housing coding features.

In a particularly advantageous embodiment, a system for a drug delivery device is provided, the system comprising:
  a housing,
  a cartridge unit, which is attachable to the housing or releasably attached to the housing, wherein the cartridge unit comprises a cartridge unit guide feature, the cartridge unit guide feature being provided to establish a guiding interface with the housing in order to guide relative movement of the cartridge unit and the housing with respect to one another when attaching the cartridge unit to the housing, and wherein the cartridge unit comprises a cartridge unit interface feature, the cartridge unit interface feature being provided to form a further interface, in addition to the guiding interface, with the housing the further interface being established when the cartridge unit is attached to the housing, wherein the guiding interface is a bayonet-type interface which defines at least two different stages of movement between the cartridge unit and the housing when the cartridge unit is attached to the housing, a first stage with at least axial movement by a first stage axial distance in a first stage axial direction and a second stage with at least rotational movement by a second stage angle in a second stage rotational direction, and wherein the further interface is or comprises a ramp interface.

As explained further above, by way of the ramp interface, an axial movement of the cartridge unit away from the housing may be achieved, preferably during the second stage. This movement may be beneficial to achieve a defined initial position between the drive mechanism, in particular, the distal end of the piston rod, and the bung in the cartridge. Alternatively or additionally coding features may be integrated into a common ramp structure with a ramp surface which establishes the ramp structure.

The terms "distal" and "proximal" as used herein may refer to opposite axial directions or ends. "Distal" may refer to a direction towards the dispensing end or an end of a component of a drug delivery device which is or is to be arranged closest to the dispensing end of the cartridge, the cartridge holder, the cartridge unit or the drug delivery device. "Proximal" may refer to a direction away from the dispensing end or an end which is or is to be arranged further away from the dispensing end of the cartridge, the cartridge holder, the cartridge unit or the drug delivery device.

The terms "axial", "radial", "angular" or "azimuthal" as used herein may be used with respect to a main longitudinal axis of the device, the cartridge unit, the cartridge, the housing or the cartridge holder, e.g. the axis which extends through the proximal and distal ends of the cartridge unit, the cartridge, the cartridge holder or the drug delivery device.

Features disclosed above in conjunction with the system, the arrangement, the drug delivery device or the set of drug delivery devices should not be regarded as referring to only the recited aspect or embodiment. Rather, the features also apply for other embodiments or aspects. Of course, features disclosed in specific embodiments, be it above or further below, can also be applied in combination with one another and/or with other features of other embodiments.

Further features, advantages and advantageous embodiments of the present disclosure will become apparent from the following description of the exemplary embodiments in conjunction with the drawings.

BRIEF DESCRIPTION OF FIGURES

FIGS. 1A through 1F illustrate an embodiment of a cartridge assembly on the basis of a schematic perspective view in FIG. 1A and a schematic sectional view of the assembly in FIG. 1B, and different views of the cartridge holder without the cartridge being arranged therein in FIGS. 1C through 1F.

FIGS. 2A and 2B illustrate one embodiment of a cartridge assembly as cartridge unit on the basis of an oblique view in FIG. 2A and a schematic sectional view in FIG. 2B.

FIGS. 3 to 13 illustrate embodiments of drug delivery devices or of systems for these devices on the basis of schematic representations.

Identical elements, elements of the same kind and identically acting elements may be provided with the same reference numerals throughout the figures.

DETAILED DESCRIPTION

Figure 1C:
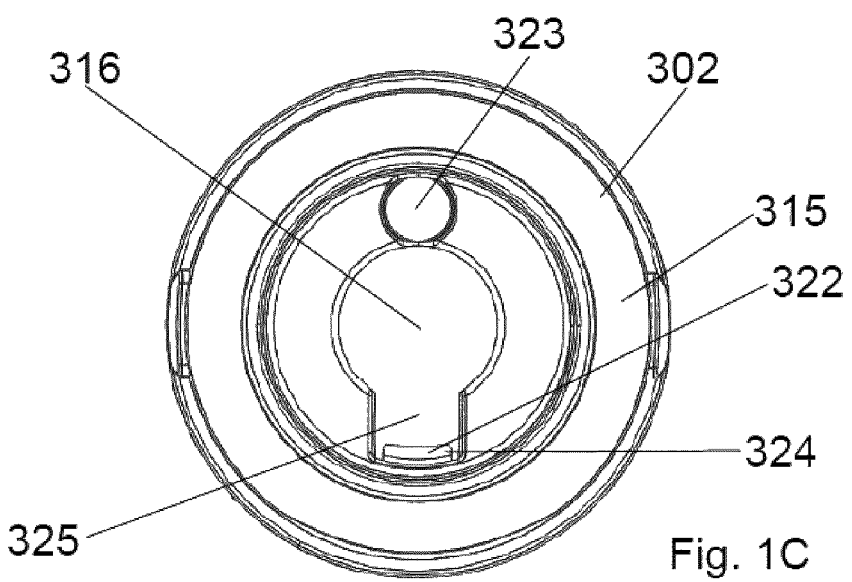
Figure 1D:
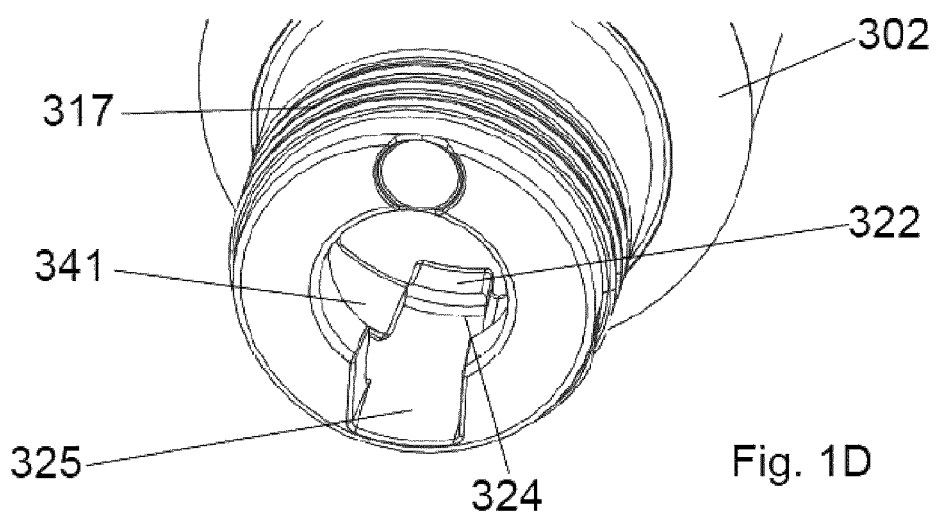
Figure 1E:
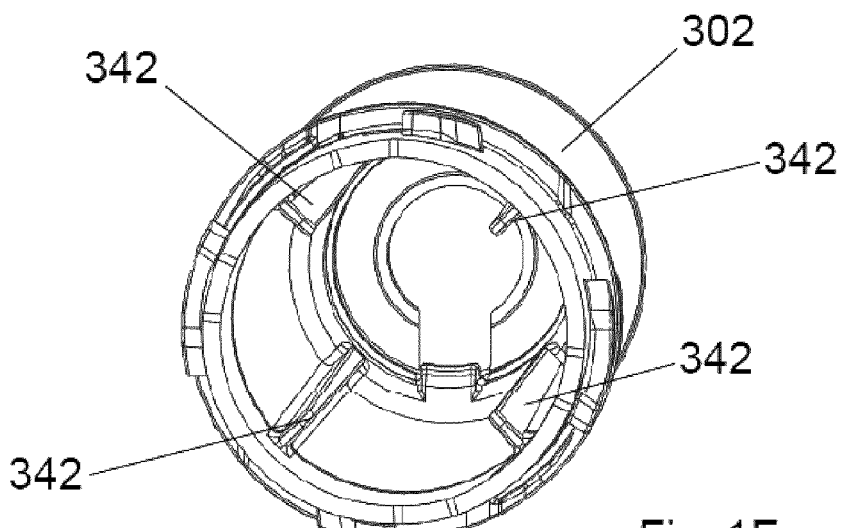

In the following, in conjunction with the FIGS. 1A through 2B, embodiments of cartridge assemblies as cartridge units are disclosed. In each case, fixing features are integrated into the cartridge holder of the unit. Before the specifics of the respective embodiments are disclosed, features which may apply to all embodiments are discussed. FIGS. 1A through 1F, as well as 2A and 2B each illustrate one embodiment of a cartridge assembly. The figure denoted with "A", in each case shows a schematic perspective view of the cartridge assembly, where in the figure denoted with "B" only the distal region, i.e. the part of the assembly close to its distal end, is shown.

The cartridge assembly 300 comprises a cartridge 301 and a cartridge holder 302. The cartridge 301 is arranged within a cartridge holding or retaining section 303 of the cartridge holder. The cartridge retaining section is expediently delimited by an inner wall 304 of the cartridge holder 302, preferably circumferentially. The cartridge holder 302 has an opening 305. The opening 305 is expediently a proximal opening. The proximal opening may provide access to the interior of the cartridge holder from the proximal end of the holder. Via the opening 305, the cartridge 301 can be inserted into the cartridge holder. A dispensing end 306 of the cartridge may be inserted or introduced into the cartridge through the opening 305. The opposite end of the cartridge holder is the distal end of the cartridge holder 302, which may be that end which is arranged closest to the dispensing end 306 of the cartridge 301. The distal end of the cartridge holder is preferably designed to retain the cartridge in the holder, e.g. by abutment, such that the cartridge may only leave the cartridge holder through the opening 305. The axial extension of the cartridge holder is expediently chosen so as to cover at least 50%, preferably more than 60% or more than 70% such as more than 80% or more than 90% of the total length of the cartridge. The entire cartridge may be covered by the cartridge holder 302 as depicted in the embodiments.

The end of the cartridge opposite to the dispensing end 306, i.e. the proximal end, is not illustrated explicitly in the figures. This end may be closed by a movable bung or stopper, which is likewise not explicitly illustrated. The bung or stopper may sealingly close a proximal opening of the cartridge. A drug 307 or medicament is contained in that region of the cartridge which is arranged between the dispensing end and the bung. Drug or medicament may be dispensed through the dispensing end 306 from the cartridge, if fluid communication between the interior of the cartridge and the exterior is provided and the bung is moved towards the dispensing end. The amount of drug 307 or medicament in the cartridge is preferably sufficient for a plurality of doses, where the size of the dose may be set by the user or may be fixed, e.g. by the design of the drive mechanism used to deliver the drug from the drug delivery device which comprises the cartridge.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids.

Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

On the side of the dispensing end 306, the interior of the cartridge which holds the drug or medicament 307 is sealingly closed by a septum 308. The septum 308 may be retained at or fixed relative to a cartridge body 340 of the cartridge by means of a septum retainer 309. The septum 308 is expediently pierceable, e.g. via a needle, which may provide fluid communication between the interior of the cartridge and the exterior. The septum retainer 309 may be formed by a cap, e.g. a metal cap, such as an aluminum cap. The metal cap may be connected via clamping or crimping to the cartridge body 340. The body of the cartridge may be formed of glass. The body 340 may define the outer contour of the cartridge. In the region of the dispensing end 306, where the needle should penetrate the septum, an opening is provided in the septum retainer 308 to allow the needle to pass through the region of the septum retainer. The cartridge 301 comprises a head portion 310 and a main body portion 311. The head portion 310 is arranged on the side of the dispensing end 306. The main body portion 311 may be arranged closer to the proximal end of the cartridge than the head portion 310. Between the head portion 310 and the main body portion 311 a neck portion 312 may be arranged. The main body portion 311 may be that region, where the bung or stopper may travel. The main body portion has a tubular configuration. The neck portion 312 may have a reduced diameter, outer and/or inner diameter, as compared to the main body portion 311. The head portion 310 has a reduced diameter, outer and/or inner diameter, as compared to the main body portion 311. The neck portion 312 has a reduced diameter as compared to the main body portion and also with respect to the head portion 310. The diameter may be the extension of the cartridge in a direction perpendicular to the main longitudinal axis of the cartridge or the cartridge assembly which extends between the proximal end and the distal end. The neck portion may extend circumferentially. The entire cartridge 301 may be rotationally symmetric relative to the main longitudinal axis. The transition between the head portion 310 and the neck portion 312 may be formed via a comparatively steep surface, which is preferably less inclined relative to the radial direction than the surface which is provided between the neck portion 312 and the main body portion 311. Accordingly, the transition between the neck portion 312 and the main body portion 311 may be less steep than the one between the head portion 310 and the neck portion 312. Specifically, a cartridge surface 313, which may delimit the head portion 310 proximally, may have an inclination relative to the radial direction which is less than the inclination of a shoulder surface 314 which delimits the main body portion distally. The cartridge surface may be formed by the septum retainer 309 or, alternatively by the cartridge body 340. The septum retainer 309 may clamp the septum to the cartridge body. Thus, the septum retainer may extend from the distal end along the cartridge to a surface of the neck portion of the cartridge body facing away from the distal end of the cartridge and extending in the radial direction to clamp the septum 308 to the cartridge body. The cartridge may comprise or consist of the cartridge body 340, the septum 308, the septum retainer 309, the drug or medicament 307, and/or the bung (not explicitly illustrated).

The cartridge holder 302 comprises on that end opposite of the opening 305 and/or closest to the dispensing end 306 of the cartridge, i.e. its distal end, a distal end wall 315. The distal end wall may extend circumferentially in a ring-like fashion. A proximal surface of the distal end wall 315 is arranged to abut the distal end face of the cartridge 301. In this way, the cartridge 301 can be retained in the cartridge holder without moving distally relative to the cartridge holder 302. The distal end wall 315 may define an opening 316 in the cartridge holder. The end wall may extend around the opening such that the opening is a central opening in the end wall. The opening may extend axially through the end wall 315. The opening 316 may be provided such that a needle can be guided through the opening towards the cartridge, in particular towards the septum 308.

The cartridge holder 302 may comprise a distal region 317 and a main body region 318. The distal region 317 is arranged closest to the dispensing end of the cartridge and/or to the distal end wall 315 of the cartridge holder. The main body region 318 is arranged further away from the distal end or the distal end wall 315 and/or closer to the opening 305 than the distal region. As compared to the main body region the distal region may have a reduced outer diameter. The reduction may be determined by the reduced diameter of the head portion as compared to the diameter of the main body portion of the cartridge. The main body region 318 and the distal region may be connected by an inwardly directed shoulder region 331. In the distal region a needle connector 319, for example a thread may be arranged. Via the needle connector, a needle unit, for example a hub of a needle unit may be secured to the cartridge holder 302. A needle retained in the needle hub may be guided through the opening 316, pierce the septum 308 and provide fluid communication to the interior of the cartridge to dispense drug or medicament 307 from the cartridge 301. The distal region 317 may be designed to receive the head portion 310 of the cartridge 301 in its interior. The main body region 318 may be designed to receive the main body portion 311 of the cartridge. On the side of the proximal end the cartridge holder may have a connection or interface region 320. In that region, connection or interface features may be provided, which are configured to cooperate with corresponding features on a housing 10 to connect the cartridge assembly 300 to the housing to form a drug delivery device 1 (see FIGS. 4 and 5). The connection features may be designed for a threaded or a bayonet connection between cartridge holder and housing. Preferably, the connection or interface features are coded to a housing which houses a drive mechanism designed for the drug contained in the cartridge of the cartridge assembly. The coding ensures that only a correct cartridge assembly can be assembled to the housing to form a drug delivery device. In this way, it can be guaranteed that the drug in the cartridge assembly is dispensed using a drive mechanism which is specifically designed to dispense the content of the cartridge. The drive mechanism may comprise a piston rod, which is arranged to drive the bung or stopper distally relative to the cartridge, if drug or medicament should be dispensed from the cartridge. An embodiment of a potential coding, which could be applied for the cartridge holder is discussed in more detail further below.

Between the proximal end and the distal end of the cartridge holder 302, preferably closer to the proximal end than to the distal end, a radially outwardly protruding step 321 or flange, may be provided. The step or flange 321 may extend over the entire circumference of the cartridge holder 302. A proximal surface of the step 321 may be arranged to contact a distal surface of the housing when the cartridge assembly is connected to the housing. The connection region 320 may be covered by the housing, when the assembly has been connected to the housing. The main body region 318 and the distal region 317 may, however, protrude from the housing.

Furthermore, the cartridge holder 301 comprises at least one fixing feature 322. As seen along the axial direction, the fixing feature 322 is provided between two interior regions of the cartridge holder, where one is adapted to receive and retain the head portion 310 and another one is adapted to receive and retain the main body portion 311 of the cartridge. The fixing feature 322 may extend in the region of the neck portion of the cartridge 301. The fixing feature 322 protrudes radially from an inner wall of the cartridge holder 301. Preferably, the fixing feature 322 reduces the inner diameter the cartridge holder such that in that region, the inner diameter is less than the outer diameter of the head portion of the cartridge.

Therefore, if the head portion of the cartridge should be guided axially past the fixing feature from the proximal opening, the fixing feature has to be deflected radially outwardly, e.g. displaced only radially. If the fixing feature is deflected, the head portion can pass the fixing feature. Preferably, the fixing feature is deflected by means of the head portion cooperating with a proximal surface of the fixing feature which may be oblique, i.e. neither perpendicular nor parallel, with respect to the main axis of the cartridge holder. After the head portion has passed the fixing feature, the fixing feature may move radially inward again, e.g. resiliently. The interior region of the cartridge holder which is designed to receive the head portion 310 may have a reduced diameter as compared to that region which receives the main body portion 311.

The fixing feature 322 is formed integrally, e.g. by injection molding, with a section of the cartridge holder which defines an exterior surface or at least the outer contour of the cartridge holder. That is to say, if applicable the cartridge holder may be provided with a coating on the exterior surface whereas the outer contour may still be defined by the section of the cartridge holder the fixing feature is integrated into. In FIGS. 1A through 4A, an injection gate mark 323 is shown, which indicates the position where the fluid plastic compound is injected into a mold cavity which defines the shape of the cartridge holder. The injection gate mark 323 is positioned in the region of the distal end wall 315 of the cartridge holder, particularly on a distal face of the distal end wall.

The fixing feature 322 comprises a fixing surface 324. The fixing surface 324 may be a distal surface of the fixing feature. Preferably, the fixing surface is radially oriented, i.e. it extends in the radial direction, and/or plane. The fixing surface 324 is arranged to abut or abuts a proximally facing surface of the cartridge, such as the cartridge surface 313. Thus, the cartridge surface 313 and the fixing surface 324 are arranged to prevent that the cartridge is removed proximally from the cartridge holder through the opening 305 by mechanical cooperation with one another. Accordingly, removal of the cartridge from the holder through the opening 305 is prevented by means of the fixing feature 322. The fixing feature 322 may be formed as a snap and/or clip feature. The angular extension of the fixing feature or the fixing surface may be less than or equal to one of the following values: 20°, 15°, 10°.

Furthermore, an outer wall of the cartridge holder is provided at the axial position of the fixing feature. Thus, the cartridge holder is closed at least in the region of the fixing feature. Accordingly, the fixing surface and/or the fixing feature cannot be accessed from the outside. This reduces the chances that the cartridge assembly can be tampered with.

In the following, some embodiments of cartridge holders with fixing features integrated into the cartridge holder are discussed in more detail. The embodiment depicted in FIGS. 1A and 1B, has one fixing feature 322, in particular just one. Of course, a plurality of fixing features could be provided as well. Such an embodiment is shown in FIGS. 2A and 2B which is very similar to the one of FIGS. 1A and 1B.

The fixing feature 322 protrudes radially from the inner wall 304 of the cartridge holder 302. The fixing feature 322 is arranged in the interior of the distal region 317 of the cartridge holder 302 and, particularly, in the interior region of the cartridge holder where the needle connector 319 is provided on the exterior. As is apparent from FIG. 1A and also from FIG. 1B, the distal end wall 315 which has a generally ring-like configuration, has an opening 325. The opening 325 is radially oriented and interrupts the ring defined by the distal end wall 315. The opening 325 extends radially outwardly from the opening 316. The angular and radial position of the opening 325 may correspond to the one of the fixing feature 322 or the fixing surface 324, where the opening is axially offset from the fixing feature, e.g. in the distal direction. Particularly, as seen from the distal end along the axis, the fixing surface may be visible from the distal end. The fixing surface may be framed radially and angularly by sidewalls which delimit the opening 325. In the figures, the head portion 310 of the cartridge 301 is arranged between the opening 325 and the fixing surface 324. The angular dimension and/or the radial dimension of the opening 325 may define, may correspond to or may be greater than the angular dimension and/or the radial dimension of the fixing surface and/or the fixing feature. Providing an opening in the region of the distal end facilitates molding of the cartridge holder with the integrated fixing feature with only minor modifications to the mold or molding tool as compared to a cartridge holder without fixing features. In a cartridge holder without a fixing feature, two core pins of different diameters may be used for producing the cartridge holder by injection molding, where one core pin defines the interior of the distal region and one core pin defines the interior of the main body region 318 of the cartridge holder. A short core pin may define the interior in the distal region and a long core pin may define the region of the interior in the main body region. The fixing feature 322 may be integrated right at the intersection or the boundary of the two different core pins of the injection molding tool. The opening 325 may be formed during the molding process and facilitates the molding of a cartridge holder with the fixing features 322 integrated into it. The opening 325 may be defined by a protrusion, e.g. of metal, on the short core pin.

In the region where the fixing feature is provided, e.g. the distal region 317, the cartridge holder may be radially deformable. Thus, the inner diameter may be increased when the cartridge holder is exposed to a radially outwardly directed force. The capability of the cartridge holder to be radially deformed when exposed to a radially directed force may be increased in that angular section of the distal region 317 which overlaps angularly with the opening 325. The fixing feature 322 is arranged in this region as it overlaps angularly with the opening. The fixing feature is expediently non-flexible and/or rigid, e.g. more rigid than the distal region 317 or the inner wall of the first region where the head portion of the cartridge is to be arranged. Thus, when an axial and/or radial force acts on the fixing feature, e.g. while the head portion is guided along and in contact with the fixing feature, the cartridge holder is widened on account of the rigidity of the fixing feature 322. The fixing feature itself is not deformed or flexed. After the head portion 310 has passed the fixing feature 322, the fixing feature is displaced inwardly again and the cartridge surface 313 and the fixing surface 324 are arranged as depicted in FIG. 1B. The fixing feature is preferably not deformed during this process and, in particular, not axially deflected or pivoted.

As shown in FIG. 1B, distally offset from the fixing surface 324, a sloped surface 326 which rises radially along its extension in the distal direction, is arranged. By means of this surface, which is preferably arranged at the opposite side of the fixing surface or at least angularly offset from the fixing surface, a radial movement of the head portion 310 of the cartridge 301 may be achieved to a region overlapping radially with the fixing surface 324. Thus, the sloped surface acts as a cartridge guiding feature during the assembling process of the cartridge assembly 300. References to the sloped surface 326 may therefore be regarded as references to the cartridge guiding feature and vice versa. The radial overlap of the fixing surface 324 and the surface 313 of the cartridge 301 when the cartridge has reached its final position may be increased in this way. The sloped surface 326 may strengthen the stability of the securing of the cartridge in the cartridge holder, e.g. in case only one fixing feature is provided.

The distal offset (highlighted with "B" in FIG. 1B) of the cartridge guiding feature 326 from the fixing feature, from the fixing surface 324 and/or from a radial free end of the fixing feature 322 may be greater than the thickness (highlighted with "A" in FIG. 1B) of the septum 308 of the cartridge. This ensures that the septum retainer 309 is backed by the more rigid cartridge body 340 and preferably not by the septum, when the cartridge interacts with the fixing feature 322 to radially displace the feature outwardly in order to temporarily widen the interior of the cartridge holder. Thus, the force required to displace the feature 322 is not transferred to the septum. If the force were transferred to the septum, the risk that the septum retainer 309, which may be a thin metal component, is deformed or the septum is damaged is considerably increased. This can be avoided by the distal offset between cartridge guiding feature 326 and the fixing surface 324 by more than the thickness of the septum 308. The distal offset B is expediently less than the axial extension of the head portion 310 of the cartridge. In this way, the cartridge guiding feature may properly guide the cartridge 301 radially inwardly by cooperating with the head portion 310.

In the region of the interior of the cartridge holder 302 between the cartridge guiding feature 326 and the fixing surface 324, the inner diameter of the interior of the cartridge holder may be greater than in the region of the cartridge guiding feature and/or in a region distally offset from the cartridge guiding feature, if such a region is present which it may be or may not be. In the region of the interior of the cartridge holder between the cartridge guiding feature and the fixing surface the inner diameter may be greater than the inner diameter in the fixing feature region. In the region of the cartridge guiding feature 326 and/or distally with respect to the cartridge guiding feature, the inner diameter of the cartridge holder may be greater than the inner diameter in the fixing feature region, e.g. greater than or equal to the outer diameter of the head portion 310.

In other words, the septum retainer or metal sleeve 309 has a distal section which surrounds the soft septum 308, and a proximal section that surrounds the neck of the cartridge body or glass ampoule 340. It is advantageous if the distal section of the septum retainer has moved past the fixing surface 324 before the distal section makes contact with the cartridge guiding feature or sloped surface 326. In this way the radial overlapping of the metal sleeve 309 and the fixing surface is minimal during the period of assembly where the fixing surface could damage the metal sleeve 309, and this overlapping is only increased when the fixing surface has moved past the distal section of the metal sleeve 309 and is applying radial pressure to the proximal section. As the proximal section is supported by a harder, e.g. glass like, material than the distal section it will not be damaged or indented. The final overlapping between the fixing surface and the cartridge surface at the end of assembling process is still high. The final overlap may be defined by the smaller inner diameter of the cartridge holder in the region of the sloped surface which marks the end of the sloped surface 326.

When a cartridge holder 302 with an integrated fixing feature 322 was tested, it has been discovered, that the distal section of the septum retainer 309 dents badly unless the diameter prior to sloped surface 326 is sufficiently larger than the diameter after slope 326 so that the cartridge 301 can move away from the fixing feature with minimal, if any, interference in the distal section of the septum retainer and that this interference only increases after the fixing feature is pressing in the region of the septum retainer 309 where the head portion of the cartridge body, e.g. of glass, backs up/supports the septum retainer, which may be a thin and easily deformable metal component.

When the cartridge 301 has been assembled into the cartridge holder 302, the fixing feature 322 may block proximal movement of the cartridge 301 relative to the holder 302. The fixing feature, however, expediently does not exert a securing force, e.g. a distally or radially directed force, onto the cartridge regularly but only prevents removal of the cartridge from the cartridge holder. In this way, the force load onto the cartridge may be advantageously low.

FIGS. 1C through 1F show additional views of the cartridge holder 302. FIG. 1C shows a view from the distal end. As is immediately apparent, the angular dimension of the fixing feature 322 is less than the one of the opening 325. The radial dimension of the fixing feature 322 or the fixing surface is less than the one of the opening 325 as well. From FIG. 1D, which shows the distal end as well but in a perspective view, it can be gathered that the cartridge holder, in particular the distal region 317, is reinforced, i.e. has a higher wall strength or thickness, in a region which is angularly adjacent to the fixing feature 322. A reinforcement section 341 extends circumferentially in the interior of the cartridge holder. The reinforcement section may axially overlap with the fixing feature. The reinforcement section 341 may be arranged distally offset from the fixing feature 322 alternatively or additionally. In the region of the interior of the cartridge holder which angulary overlaps with the fixing feature the reinforcement section is preferably interrupted to promote radial deformability of the cartridge holder when the head portion displaces the fixing feature 322 radially.

Figure 1F:
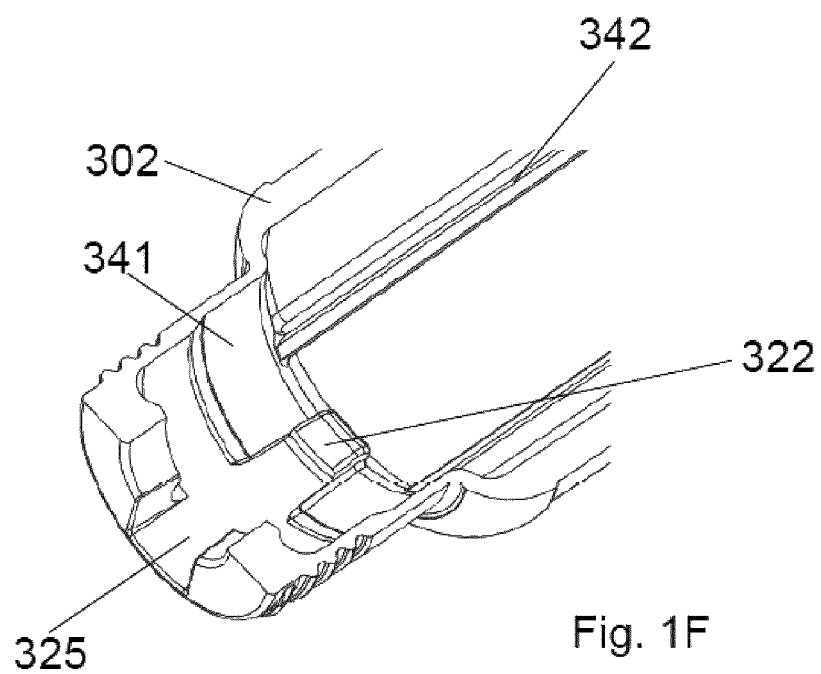

As seen from the opening 325 axially towards the fixing surface 324, the wall thickness of the holder 302 may be less than the wall thickness in the reinforcement section 341. The wall thickness of the cartridge holder 301 in the region of the fixing feature 322 and defined by the fixing feature may be greater than the one in the reinforcement section 341. The fixing feature 322 may radially protrude over the reinforcement section 341. The reinforcement section 341 is also depicted in FIG. 1F which shows a perspective sectional view of the cartridge holder 302. In this figure as well as in FIG. 1E, which shows a view from the proximal end of the cartridge holder 302, it is shown that the interior of the cartridge holder comprises a plurality of circumferentially disposed, preferably equally spaced, spacer features or cartridge support features 342, e.g. ribs. The features 342 are axially oriented. The features 342 may be provided to radially support the cartridge, e.g. the main body portion 311 thereof, if the cartridge is retained in the cartridge holder. These features may be the only difference between a cartridge holder which receives cartridges with a smaller diameter and one which receives a cartridge with greater diameter. The cartridge holder for the larger diameter cartridge may, expediently, not have the cartridge support features 342. Thus, the exterior dimensions of the cartridge holder may be the same although the exterior diameters of the cartridges retained in the cartridge holders are different.

As is apparent from the figures, e.g. from FIG. 1B, the needle connector 319, e.g. a thread, is distally offset from the fixing feature 322. Specifically, the region between the fixing feature and the cartridge guiding feature or sloped surface 326 may be free of the needle connector 319. The needle connector may axially overlap with the cartridge guiding feature 326 or be provided distally offset from this feature 326. Thus, the axial extension of the needle connector 319 may be less than in other cartridge holder designs. For example, the needle connector 319 may be restricted to a distal section of the distal region 317 of the cartridge holder, where between the needle connector 319 and the main body region a connector-free region is arranged. The axial extension of the connector-free region may be greater than 50% of the axial extension of the distal section with the needle connector. The axial extension of the distal section with the needle connector may be greater than the one of the connector-free region. As the cartridge holder in the region between the fixing feature 322 and the guiding feature 326 has a reduced wall thickness to increase the inner diameter of the cartridge holder 302, e.g. in order to maintain a given outer contour or dimension of the cartridge holder 302, providing an additional radial indentation on the exterior in this region, which would be required for the connector 319, would increase the risk of damaging the cartridge holder in this region or even render it unmoldable. Thus, the shortened needle connector is advantageous.

Although the depicted embodiment shows only one fixing feature, a sloped surface may also be provided in case a plurality of fixing features is used. In the following embodiment, the sloped surface is not shown, however.

In FIGS. 2A and 2B a cartridge holder 302 with two integrated fixing features 322 is shown. The fixing features 322 are oppositely disposed where each fixing feature has a fixing surface 324 which is arranged to abut the fixing surface 313, which may be formed flange-like. Two openings 325 are provided in the distal end wall 315 of the cartridge holder which interrupt the ring-like shape of the cartridge holder at positions which angularly and/or radially correspond to the position of the fixing surface 324 of the respective fixing feature. The respective opening 325 may be connected to the central opening 316. As explained previously, this assists in integrating the fixing feature into the cartridge holder by injection molding which is particularly easy and a low-cost process, suitable for high volumes. The disclosure above regarding the opening therefore also applies for this embodiment. Still further, more than two fixing features could be provided as well. In FIG. 2B, the needle connector overlaps axially with the fixing feature(s) 322.

As the fixing feature 322 interacts with the head portion in the depicted embodiments, cartridges with differently shaped main body portions may be secured in the cartridge holder easily, e.g. cartridges of different volumes, such as 1.5 mL and 3 mL, different diameters and/or lengths. The head portions of the cartridges may be formed alike.

It should be appreciated that the present disclosure is particularly advantageous for cartridge assemblies with cartridges which are permanently secured therein as cartridge units. However, also cartridge holders with removable cartridges where the cartridge can be replaced in the cartridge holder can be used as cartridge units in the presently disclosed concepts.

Cartridges of different volumes may have different lengths and/or different inner and/or outer diameters. The cartridge assembly may be a disposable item, which is e.g. sold in the pharmacy. Different cartridges of the same or of different volumes may contain different drugs or drug formulations. Cartridges of a smaller volume may have a higher concentration of a drug. If the drug is insulin or an insulin derivative, for example, the cartridge of a smaller volume may have a concentration which is more than 2 times, e.g. 3 times, the concentration of drug or medicament in the larger volume cartridge. The drug in the larger volume cartridge may be formed by the same active pharmaceutical ingredient. Differences in the content between the cartridges may be, preferably only, in the concentrations of the drug within the liquid, i.e. in the specific formulation of the drug. For example, a 3 mL cartridge may comprise 300 IU (IU: International Unit), e.g. of insulin, whereas the 1.5 mL cartridge may comprise 450 IU, which, taking into account the lower volume, corresponds to three times the concentration of drug in the 3 mL cartridge.

In reusable drug delivery devices, where the same drive mechanism can be used in conjunction with several cartridges, it is extremely advantageous to ensure that only cartridges with a specific drug or drug formulation can be operatively connected to the drive mechanism, e.g. connected to a housing within which the drive mechanism or elements thereof are retained. This is, sometimes, achieved by so-called coding or dedication systems or mechanisms. These systems or mechanisms may comprise features which are adjusted such that in a set of two drug delivery devices, each comprising a housing with a dose setting and/or drive mechanism and a cartridge unit releasably connected to the housing, where the two cartridge units have different drugs, drug formulations and/or dimensions, the respective cartridge unit can only be connected to the housing of one device and not to the housing of the other device.

In the following text, embodiments of systems are described, which are suitable for uniquely coding cartridge units or assemblies with specific drugs, drug formulations and/or cartridge dimensions or volumes to housings or the dose setting and/or drive mechanisms retained therein. This avoids that the wrong mechanism can be used in conjunction with a particular cartridge unit, e.g. one of the assemblies discussed further above. The disclosed embodiments are particularly suitable for being used for drug delivery devices which employ a bayonet or bayonet-type connection between the cartridge unit and the housing, which involves an initial at least axial movement (first stage) and a subsequent at least angular or rotational movement (second stage) when attaching the cartridge unit to the housing. Additionally the disclosed concepts are designed to achieve an axial movement of the cartridge unit away from the housing after the first stage and before the end position of the cartridge unit with respect to the housing has been reached.

Figure 3:
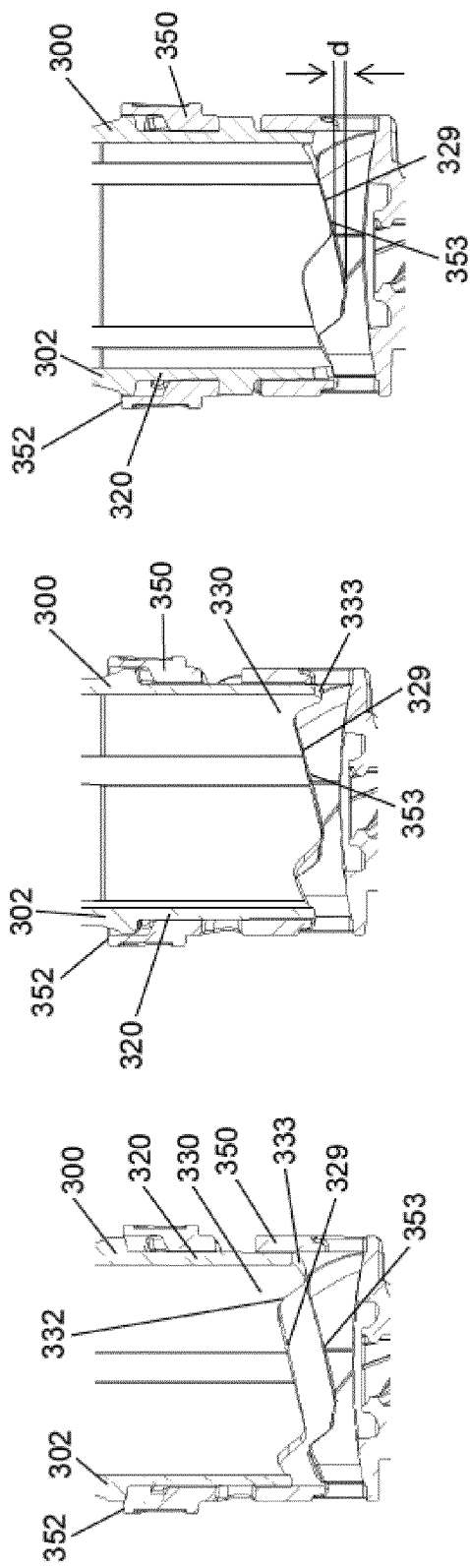
Figure 3:
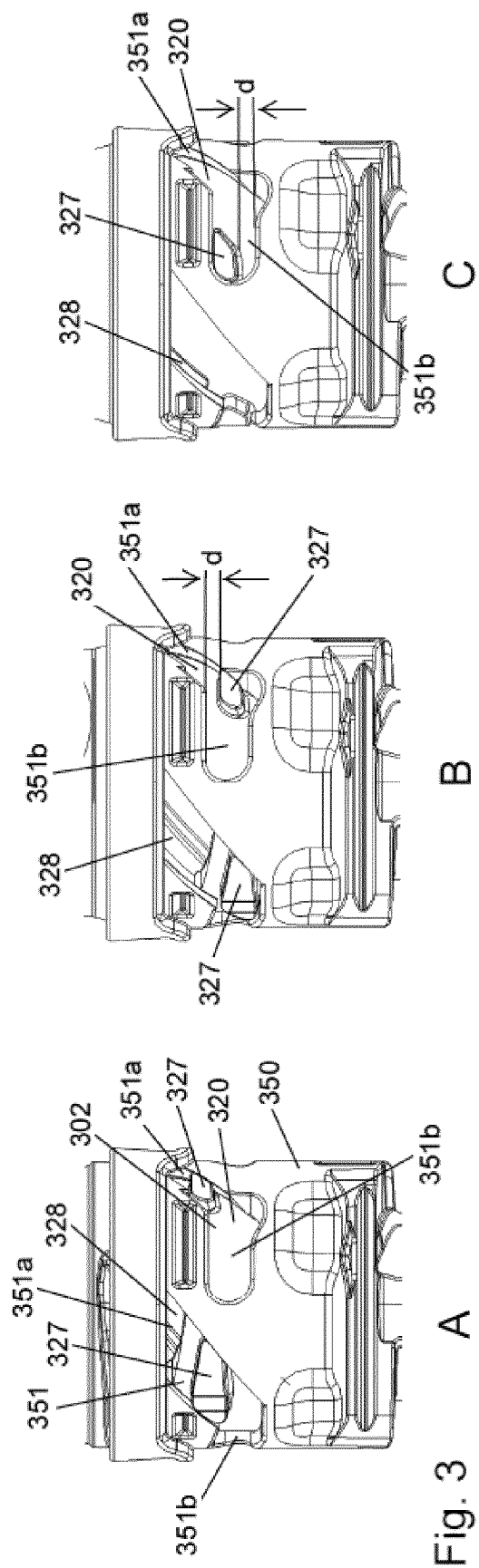

One embodiment is discussed below in conjunction with FIG. 3. FIG. 3 schematically illustrates different situations (A through C) during the connection of a cartridge unit 300 to a housing or housing part 350 for a drug delivery device. Situation A is shortly after the connection or attachment has begun, i.e. during the first stage of movement, situation B is after the first stage of movement has been completed and before the second stage of movement begins, and situation C is when the end position of the cartridge unit 300 relative to the housing has been reached after the second stage of movement has been completed. The lower portion of the figure shows side views in the situations A through C and the upper portion shows sectional views in the associated situation.

The cartridge unit 300 is represented by a cartridge holder 302, e.g. one of the holders described previously. Of course, although not depicted, the cartridge may be present in the cartridge holder. In FIG. 3, the connection region or interface region 320 of the cartridge holder is shown. In this region, one or more features are arranged which are adjusted to interact with features in a housing when connecting the cartridge holder 302 or the cartridge unit or assembly 300 to the housing to form a drug delivery device. In particular, in the connection or interface region 320, one guide feature 327 or a plurality of guide features 327 is arranged. Different guide features 327 may be axially aligned and angularly separated from one another. The guide features may have different angular or azimuthal widths as depicted or the same angular or azimuthal widths. The guide features 327 are provided to guide movement of the cartridge holder 302 relative to the housing during assembling or attaching of the cartridge holder 302 to the housing. The cartridge holder 302 may, in particular in the connection or interface region 320, comprise a securing or detent feature 328. A plurality of securing features 328, where only one of them is shown, may be provided which are preferably uniformly disposed in the angular direction, e.g. diametrically opposite with respect to one another. The respective guide feature 327 may be realized as a lug protruding from the cartridge holder 302. The securing feature 328 may have a helical shape or extension. The securing feature 328 may be designed to releasably secure the cartridge holder in the end position against rotation relative to the housing in the direction required for detaching the cartridge holder 302 from the housing. This avoids accidental disconnection of the cartridge holder from the housing.

The housing part 350 may be integrally formed with an (outer) housing 10 of a drug delivery device as explained later on or as an additional component mounted in or at the housing. The housing part 350 comprises at least one, preferably a plurality of housing guide features 351. The housing guide feature 351 may be a track or channel. The housing guide feature 351 comprises two different sections, a first section 351a and a second section 351b. The first section 351a extends at least predominantly axially, such as only axially or helically. In the depicted embodiment it extends helically. The helix angle of the helix along which the first section 351a extends may be the same as the one defined by the helical extension of the securing feature 328. The axial distance between two opposite ends of the section 351a may be greater than the angular extension of the first section. For example the midpoints of the respective end can be taken as reference points for measuring the distances separating the ends.

The housing part 350 has a distal end 352. Before the cartridge holder 302 is assembled to the housing part 350, the distal end 352 may face the cartridge unit 300. The housing part 350 may be hollow, e.g. formed sleeve-like, in order to enable components of the drive mechanism and/or of the cartridge assembly to be received within an opening of the sleeve member or to travel through the opening. The section 351a is expediently arranged closer to the distal end of the device or the housing than the second section 351b of the housing guide feature 351. The second section 351b of the guide feature 351 may extend at least predominantly angularly, such as only angularly or helically. Particularly, the axial distance between opposite ends of the second section may be less than the angular extension of the second section. The axial distance the cartridge holder is moved in the first section may be greater than the axial distance it is moved in the second section. Alternatively or additionally, the angular distance the cartridge holder is moved in the first section may be less than the angular distance it is moved in the second section. The axial distance the cartridge holder is moved in the second section or during the second stage may be less than or equal to 1 mm, e.g. less than or equal to 0.5 mm. The guiding interface may be a bayonet-type interface. The rotational directions in the first stage and in the second stage may be equal.

In the depicted embodiment, the first section 351a extends helically or is configured to define a helical interface. The second section 351b may extend only angularly or helically and/or be configured to allow a, preferably limited, axial movement. Thus, there may be some axial play in the second section. This preferably holds, if the second section extends only angularly (see section 351b in FIG. 3C). The play may allow a movement of the cartridge holder 302 away from the housing 350 during the second stage as will be explained below. If the second section extends helically (see the leftmost section labelled with 351b in FIG. 3A) an axial play may not be present. Particularly, as is shown in the figures, different housing guide features 351 may have differently configured second sections 351b, e.g. the second section of one housing guide feature may extend helically and the second section of another one may extend only angularly. The first sections of different housing guide features may be formed alike. The first section 351a of the housing guide feature 351 may guide the movement during the first stage, e.g. axially and/or angularly, whereas the second section 351b of the guide feature may guide, preferably only, angular or rotational movement of the cartridge holder relative to the housing. Nevertheless, during the second stage of movement, there may still be an axial component of the movement of the cartridge unit away from the housing. For this purpose, a further interface is established which will be explained in more detail below. Thus, as axial and angular or rotational movements are involved when the cartridge unit guide feature 327 interacts with the second section 351b of the housing guide feature 351, the movement may still be helical in this section. The helix angle of the helix associated with the movement during the second stage or the second section may be less than the one associated with the first section or the first stage. Alternatively or additionally the helixes which define the helical extension of the respective sections 351a and 351b or the helical movement during the two stages may be oriented in opposite directions, e.g. they may be oppositely handed. In this way, while the guide feature 327 is in the second section, the cartridge holder may travel in the distal direction relative to the housing, i.e. opposite to the axial direction it travels in when the movement is guided in the first section. Thus, when the guide feature 327 interacts with or travels in the first and second sections of the guide feature 351 different stages of movement occur. A mechanism which has an initial proximal movement of the cartridge holder towards the housing which is followed by a distal movement away from the housing is disclosed in WO 2012/130704 A1, the entire disclosure content of which is herewith incorporated by reference into the present application. However, the proposed concepts are applicable to other, preferably reusable, drug delivery devices as well, e.g. to injection devices such as pen-type injectors.

As mentioned above already, the axial movement away from the housing during the second stage of movement may be generated by a further interface, i.e. by an interface different from the guiding interface established by the cooperating guide features 327 and 351. This interface may be a ramp interface. For this purpose, the cartridge holder, e.g. at its proximal end, comprises at least one ramp surface 329 or a plurality of ramp surfaces. The housing comprises at least one corresponding ramp surface 353 or a plurality thereof. The ramp surfaces 353 and 329 do not interact during the first stage of movement (situation A), are brought into cooperation with one another at the end of the first stage (situation B), i.e. after the cartridge holder has been moved by a first stage axial distance towards the housing, and interact with one another during the second stage (situation C). The slope of the ramp surfaces 353 and 329 may be equal.

However, it should be readily appreciated that one ramp surface is sufficient and the feature sliding along the ramp surface may have a different, i.e. not necessarily ramp-like, geometry. The slope of the ramp surface is preferably constant. The slope of the ramp surface may be chosen such that during the rotational movement during the second stage the ramp surface causes the axial movement by the distance d away from the housing (which takes place from situation B to situation C). As can be seen, in situation B, the axial clearance between the guide feature 327 and the wall delimiting the guide feature section 351b distally may be equal to the distance d. At the end of the attachment process in situation C a distally facing surface of the guide feature 327 and a proximally facing surface of the housing may abut. In situation C, the distance between a proximally facing surface of the guide feature 327 and of a distally facing surface of the housing may be greater than or equal to d. In situation C, when the cartridge holder has been attached to the housing, the securing feature 328 has engaged a complementary securing feature in the housing (not illustrated). The rotation angle during the second stage may be greater than 10° and/or less than 90°, such as less than 45°, e.g. about 20°.

The angular extension of the ramp surface 253 and/or 329 may be greater than the rotation angle during the second stage. This enables that a section of the ramp surface, e.g. of the ramp surface 253, can be used to abut a coding feature, e.g. of the cartridge holder, if a cartridge holder with a non-matching coding structure is attempted to be attached to the housing. This will be explained later below.

The cartridge holder 302 comprises one or a plurality of coding features 330. The coding feature may be oriented axially. The coding feature may be integrated with the ramp surface in a common ramp structure. The coding feature comprises a surface 332 which delimits the coding feature in the angular direction, e.g. that angular direction opposite to the direction of rotation during the first stage and/or during the second stage. Rotation of the cartridge holder 302 relative to the housing part 350 during the first stage and the second stage is clockwise as seen from the distal end towards the proximal end in FIG. 3. The surface 332 may extend axially and/or, as seen in the axial direction, overlap with the ramp surface 329. The surface 332 may have an axial extension, which is greater than d, greater than the axial distance during the first stage and/or during the second stage and/or greater than the axial extension of the ramp surface 329 and/or 353. The angular extension of the surface 332, if any, is expediently less than the one of the ramp surface 329 or 353. By choosing the axial extension greater than the axial distance covered during the first stage and/or during the second stage, a proximally facing surface 333 of the coding feature 330, which adjoins the surface 332 angularly, e.g. in the rotational direction during the first stage and/or the second stage, may be used to abut the ramp surface 353 or another distally facing surface in the housing, which is provided by a housing coding feature, in case the cartridge holder is attempted to be attached to a non-matching housing. This abutment prevents further axial movement of the cartridge holder towards the housing and, accordingly, the second stage cannot be performed and the cartridge holder cannot be attached to the housing. The coding therefore acts during the first stage of movement, i.e. as early as possible, to alert a user if he or she attempts to attach an incorrect cartridge unit to the housing. When the length of the surface 332 is significantly greater than the axial distance during the second stage or dimension 'd', e.g. at least twice the axial distance, it can be ensured that the coding feature 330 can block the attachment of the cartridge holder early during the first stage, if the cartridge holder and the housing do not match. Alternatively or additionally, it may be beneficial, if the length of the surface 332 is greater than the axial distance during the first stage.

Using ramp structures in the housing or on the cartridge holder enables a robust and easy to implement coding structure with a variety of differently formed and/or arranged coding features, which form unique coding structures together with ramp surfaces or ramp features into a common ramp structure. In other words, the coding features and the ramp surfaces may be axially aligned and angularly separated. Such structures can be easily incorporated in existing holders without extensive changes to the expensive molding tools.

The ramp structures used in the present disclosure may be formed rotationally symmetrical with respect to a rotation by 180°. In this way, the cartridge holder may be connected to the housing in two different rotational orientations. Likewise, the guide features may be arranged rotationally symmetrical, particularly with respect to a rotation by 180°.

The ramp surfaces of the ramp structures used in the present disclosure may be separated by coding features arranged between them. The transition between the coding feature and the subsequent ramp surface may be formed by a steep axially oriented surface or by a sloped surface. The (angular) slope in the transition region between two ramp surfaces may be greater than the slope of the ramp surface.

Figure 4:
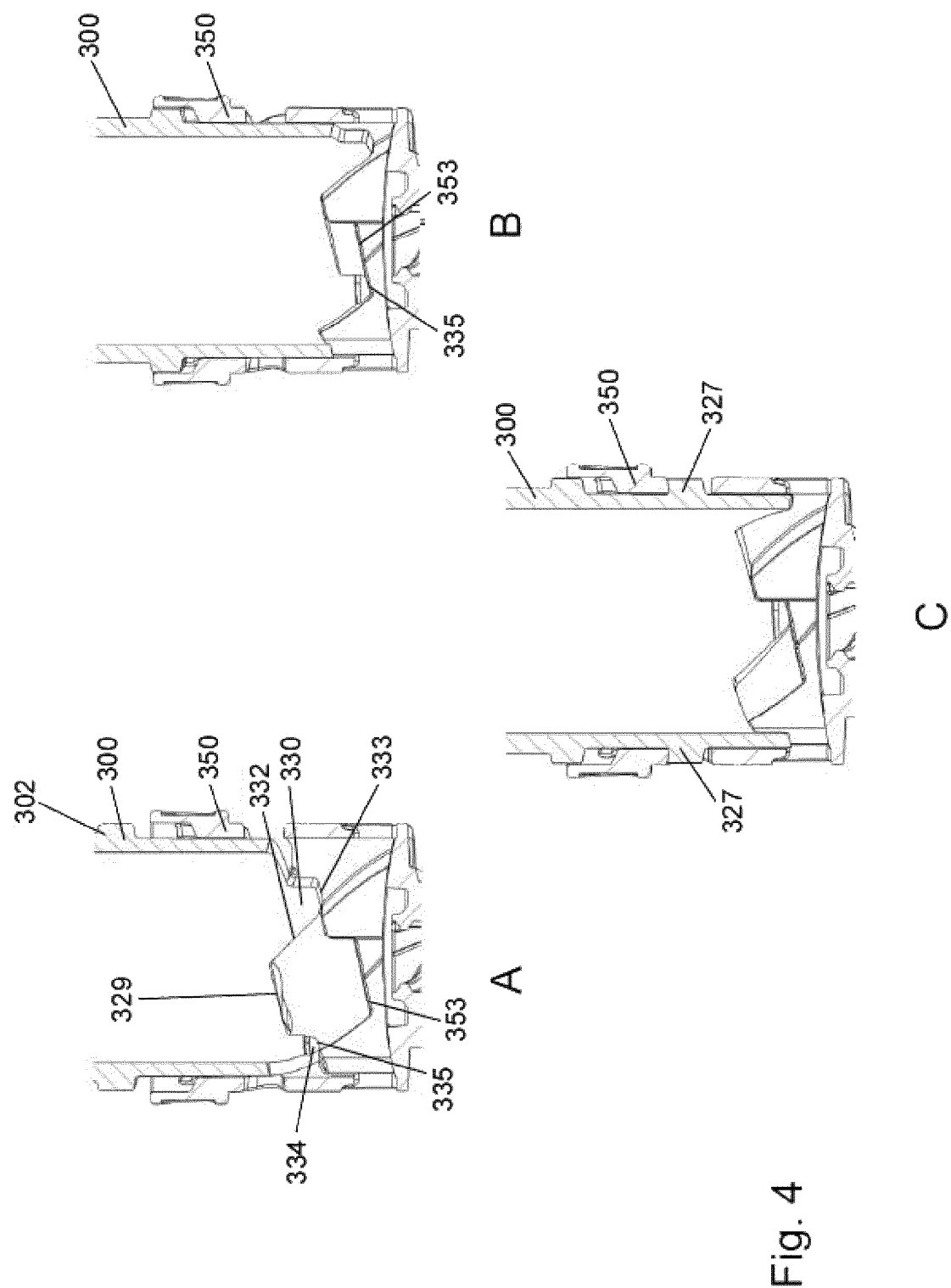

FIG. 4 shows an embodiment of a cartridge unit and a housing with matching ramp or coding structures which utilizes a different ramp or coding structure than the previous embodiment. Again the cartridge unit 300 and the housing are shown in different situations A through C, but only in sectional views as the guiding functionality may be the same. In the following, only the differences to the previously described embodiment are discussed.

A key difference is that the cartridge holder 302 does not comprises a ramp surface or at least not one of significant angular extension which interacts with the ramp surface of the housing during the second stage of movement. Rather, for interaction with the ramp surface 353 in the housing the cartridge holder comprises a ramp interaction feature 334. A proximally facing surface 335 of this feature 334 contacts the ramp surface 353, expediently before the second stage, e.g. at the end of the first stage (situation B). The feature 334 may slide along the ramp surface 353 during the second stage (situation C). At the end of the attachment procedure a surface which delimits the feature 334 in the angular direction, expediently the direction of rotation during the second stage, may angularly abut a feature which delimits the ramp surface 353 in the angular direction. This may provide a robust rotational end stop, in addition or as an alternative to an end stop provided by the guiding interface formed by the guide features 327, 351. The angular extension of the ramp surface 353 may be greater than or, as depicted, equal to the sum of the angular extension of the surface 335 and the angular extension defined by the rotation angle during the second stage along the ramp surface. It should be appreciated that the interaction feature could as well be positioned on the housing and the ramp surface on the cartridge holder. The slopes of the ramp surfaces in the FIG. 4 and FIG. 3 embodiments are equal such that they can generate the second stage axial movement by the distance d. As is immediately apparent the ramp structure in the housing is adjusted to the cartridge holder to provide a matching pair of cartridge unit and housing. The cartridge holder 302 may nevertheless comprise a ramp surface 329, which may abut a feature of the housing during the second stage. Ramp surfaces 329 and 353 may have the same slope as is depicted. If applicable the ramp surface 329 may be sufficient and the ramp surface 353 can be dispensed with.

Therefore, with the same guiding interface but different coding and/or ramp structures it can be prevented that non-matching cartridge holders are attached to a housing, where the ramp surfaces of the ramp structures may effect or generate the axial movement during the second stage.

Figure 5:
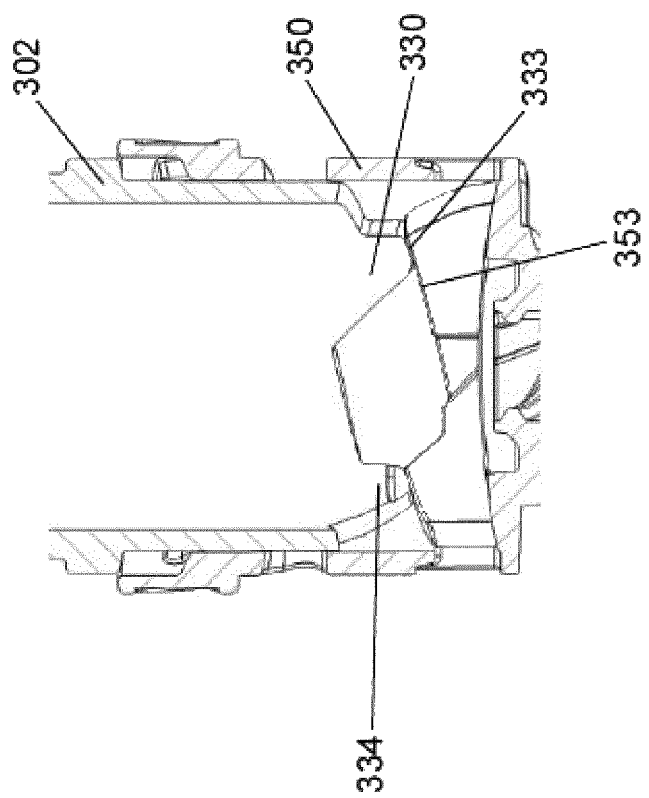

FIG. 5 illustrates that the cartridge holder of FIG. 4 cannot be attached to the housing of FIG. 3. While still in the first stage of movement, the surface 333 of the coding feature 330 abuts the ramp surface 353, e.g. an end section thereof, such as seen in the angular direction of rotation during the first stage. Therefore, further axial and/or rotational movement is prevented and the cartridge holder cannot be attached to the housing. Thus, on account of the different ramp structures which comprise ramp surfaces of equal slopes and the different designs and arrangements of the coding feature(s) attachment of the cartridge holder to the housing is prevented, preferably still during the first stage of movement. This holds although the same guide features 327 and 351 for the bayonet-type connection movement are present in the FIG. 3 and the FIG. 4 embodiments.

Figure 6:
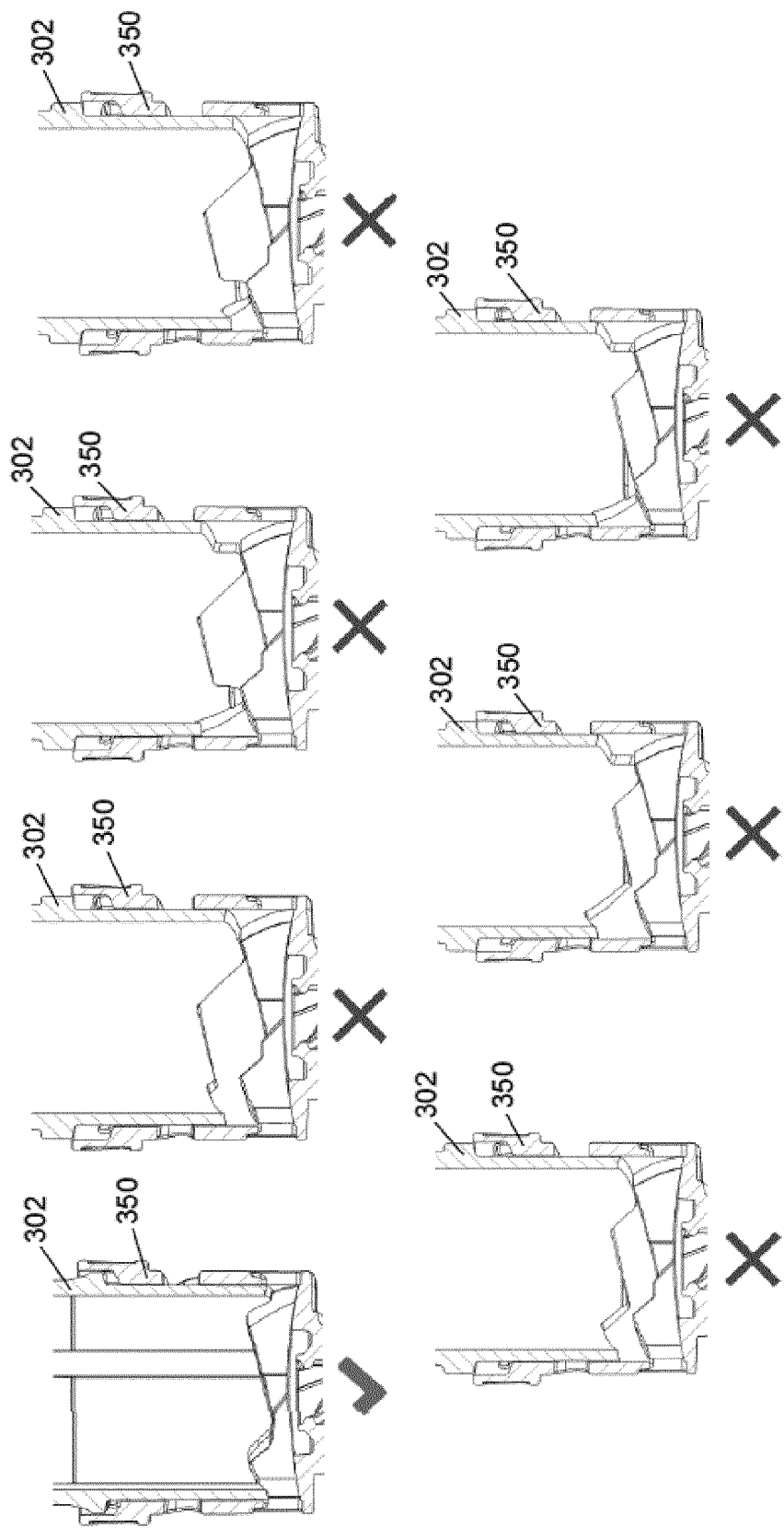

FIG. 6 shows a range of seven different cartridge holders, all of which have ramp or ramp structure geometries. These are all shown in conjunction with the housing or housing part 350 of FIG. 3, i.e. the ramp structure in the housing is always the same. It can be seen that only one of the holders (the same embodiment shown in FIG. 3 and indicated by the hook (tick mark) below the representation of the cartridge holder and the housing) is coded to be compatible with the housing, meaning that only one can be attached to this housing. In the other representation—i.e. the ones highlighted with an "X"—the coding features of the cartridge holder come into contact with the coding features of the housing, e.g. with the ramp surface 353—before the first stage of, e.g. helical, movement is completed. For each of the six non-compatible cartridge holders, a compatible housing component can be created which is in turn not compatible with all of the other cartridge holders. In this way a set of, e.g. up to seven or up to ten, a plurality of coded cartridge holders can be provided; each one being only compatible with a particular housing or drive mechanism. All of the shown systems do have ramp surfaces of the same slope.

Figure 7:
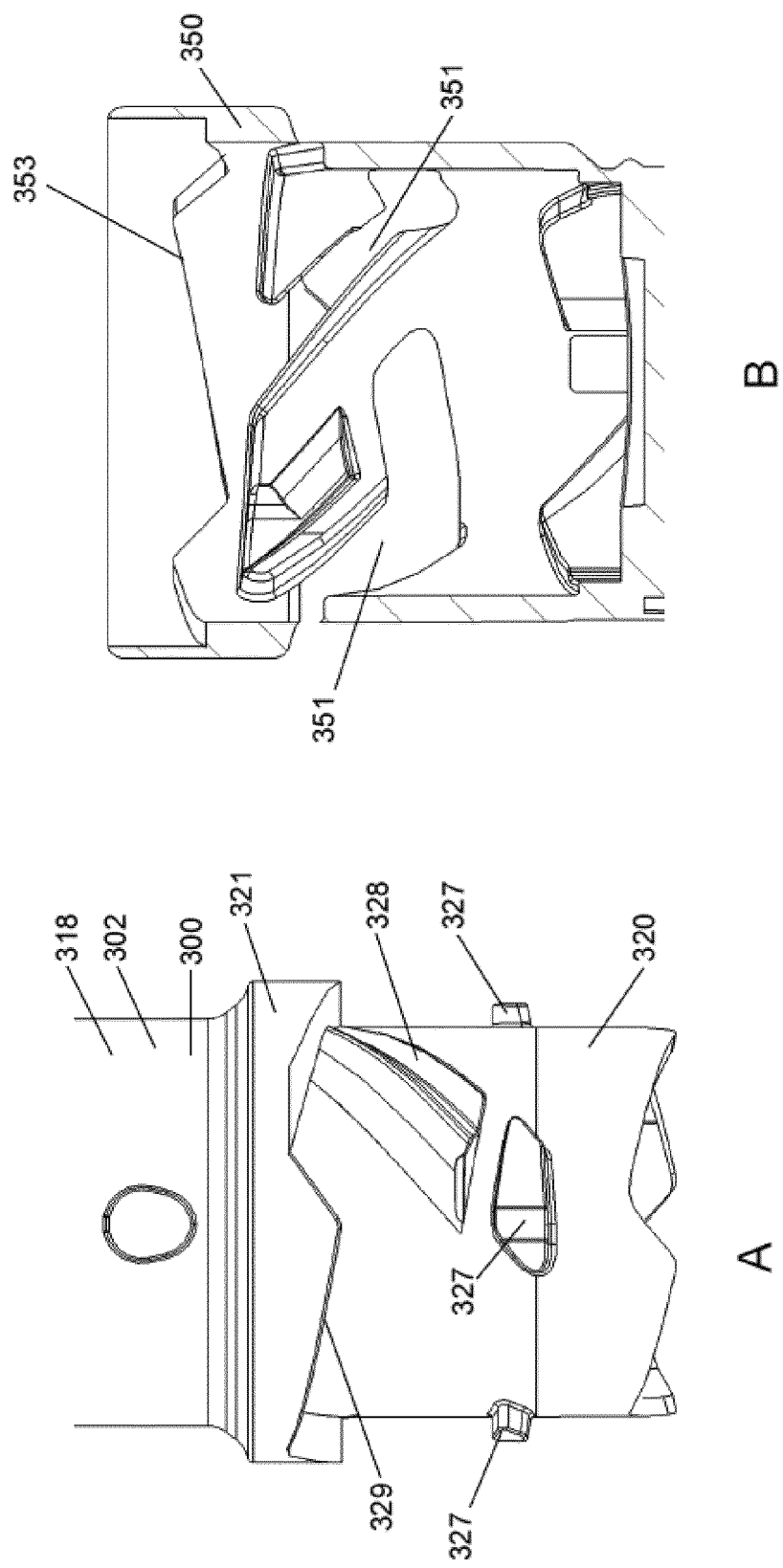

FIG. 7 illustrates another embodiment of a cartridge unit 300 (labelled A) and a housing or housing part (labelled B). The housing or housing part 350 is shown in a sectional view and the cartridge unit is shown in top view. As opposed to the previous embodiments, the ramp structure which provides coding functionality and/or the movement by the second stage axial distance, is not arranged at the proximal end or rim of the cartridge holder. Rather, it is provided on or in the proximally facing surface of the step 321. The step is arranged between the main body region 318 of the cartridge holder 302 and the interface region 320, where the guide features 327 and the securing feature 328 is arranged. Thus, as opposed to the previous embodiment where it was proximally offset, particularly integrated into the proximal rim or edge of the cartridge holder, the ramp structure may be distally offset from guide features 327 and/or the securing feature 328. Further, the corresponding ramp structure in the housing is provided distally offset from the guide features 351. The remaining functionality is the same. As the step may be provided in an already existing device, the ramp structure can be easily implemented on the proximal surface of the step 321.

Figure 8:
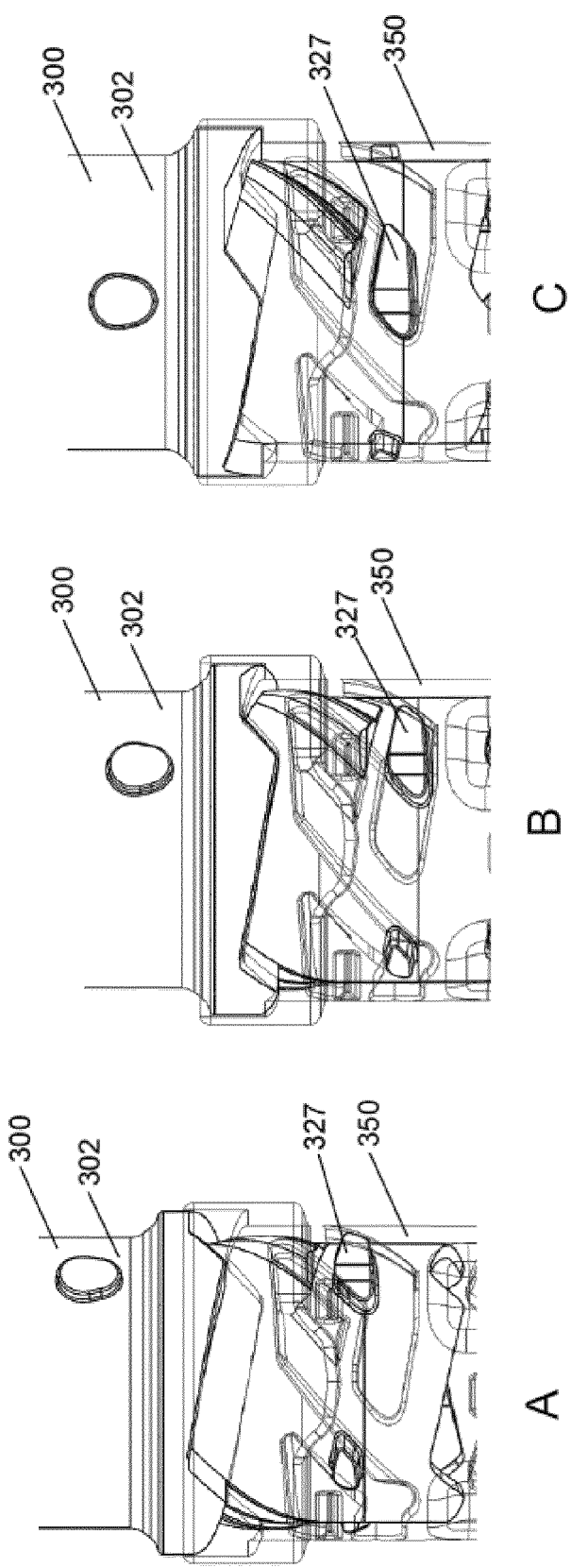

FIG. 8 illustrates the attachment sequence of the cartridge holder 302 and the housing or housing part 350 of FIG. 7 in three different situations (labelled A through C), which correspond to the ones discussed further above. As the ramp structures match one another, the cartridge holder can be attached to the housing. The ramp features or surfaces of the shoulder or step 321 function in the same way as the ones discussed previously. By adjusting the geometry of the ramps of the cartridge holder in the same or in a similar way to that discussed above with reference to FIGS. 3 to 7, a set of coded cartridge holders and housings can be created.

Figure 9:
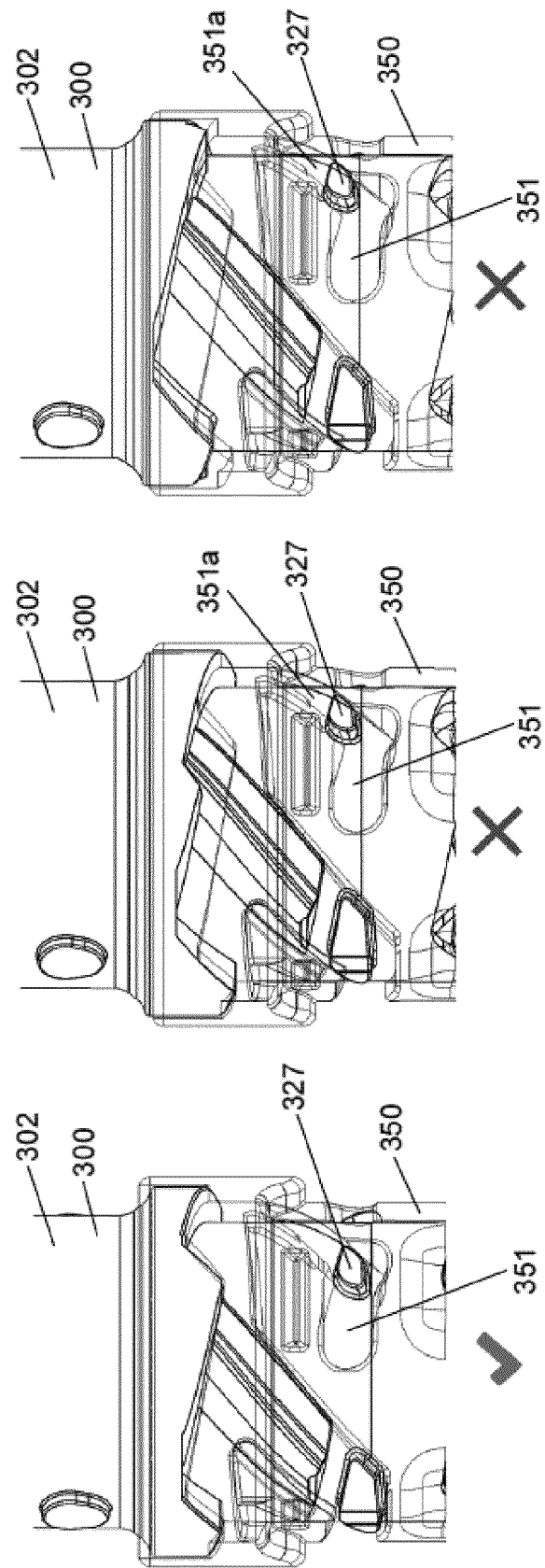

FIG. 9 illustrates three pairs of housings or housing parts 350 and cartridge holders 302, where the housing always has the same ramp structure and the ramp structures of the cartridge holders vary. The pair on the left has matching ramp structures (indicated by the hook or tick mark) and the other ones have not (indicated by the "X"). As is apparent form the two pairs on the right, the axial movement towards the housing is stopped due to the non-matching ramp structures before the second stage of movement can occur, i.e. the guide feature is still in the first section 351a when the further movement is blocked.

FIGS. 10 and 11 illustrate another coding structure which is suitable to be used together with a bayonet-type connection between the cartridge holder and the housing. FIG. 10 shows the cartridge holder 302 when it has been connected to the housing or housing part 350. The guide feature 351 of the housing, again, has two sections 351a and 351b, where, in contrast to the previously described embodiments, the first section extends only axially and the second section only angularly. The guide feature does not have a helically extending section. Thus, in the first stage there is only axial movement and in the second stage there may be only angular movement as in the depicted embodiment, where the guide feature 327 has the same axial dimension as the second section 351b or angular and axial movement, preferably helical movement as will be described further below. The latter allows for the axial movement of the cartridge holder 302 in the distal direction during the second stage. After completion of the second stage, as described previously, the cartridge holder 302 is secured against rotation relative to the housing or housing part 350.

The coding functionality for the cartridge unit is implemented by the guide features 327 or lugs which simultaneously act as coding features. By varying the angular widths—wide features 327a and narrow features 327b—and/or the relative angular positions of the preferably axially aligned guide features 327 together with appropriately designed guide features 351 in the housing for a matching housing, the coding can be realized. One sort of guide features—wide or narrow—can stay at the same angular position where the position of the narrow guide features may be varied. FIG. 11 shows potential lug feature locations for a range of five different cartridge holders 302 when viewed in each case from the open end of the cartridge holder. It can be seen that on every holder 302 there are two sets of lugs or guide features, a first set of oppositely disposed 'wide' lugs and a second set of oppositely disposed 'narrow' lugs. It can also be seen that the wide lugs are located in the same angular position in each variant, whereas the narrow lugs are rotated to a different angular position with respect to the wide lugs in each instance. This arrangement of lugs provides a set of codes, which means that each different cartridge holder variant will only be engageable with a housing that has channels or guide features 351 located at the same angular position as the guide features or lugs of the matching cartridge unit.

Figure 12:
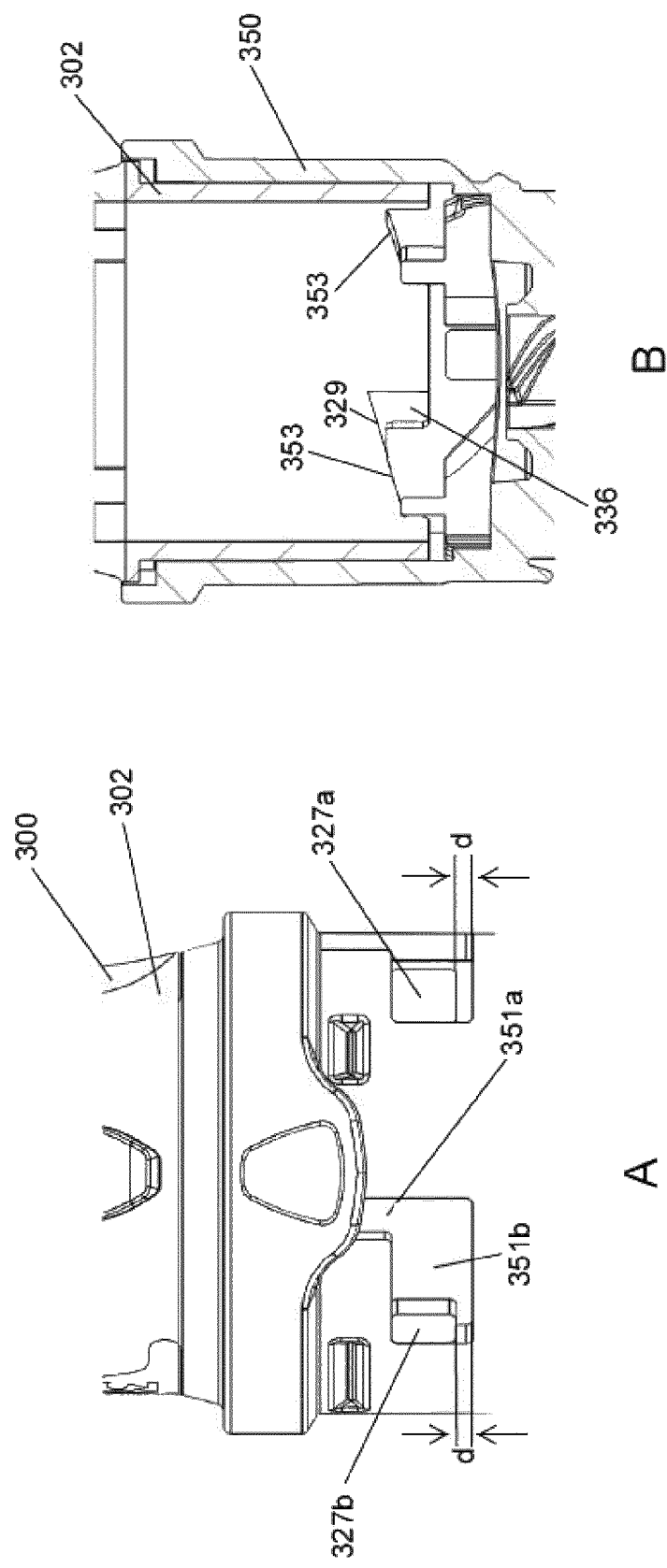

As opposed to the ramp structures with the integrated coding features discussed further above, this coding structure which uses the angular width and/or position of the guide features does not provide the axial movement of the cartridge holder away from the housing during the second stage. A potential solution to this problem could be to introduce helical channels for the second region of travel, i.e. helical second sections 351b. However, these might be difficult to mould in the body component. An alternative solution that is likely simpler to manufacture is shown in FIG. 12. The representation A in FIG. 12 shows a side view when the cartridge holder 302 has been assembled to the housing and representation B shows a sectional view. As can be seen, the second section is axially wider than the axial extension of the guide feature to permit the distal displacement of the cartridge holder relative to the housing, e.g. by the distance d, during the second stage of movement. The housing or housing part has one or more ramp surfaces 353. These surfaces may interact with the cartridge holder 302 and lift the cartridge holder 302 axially away from the housing during the second stage of movement. In the end position, there may be an angular clearance 336 between axially overlapping angular surfaces of the cartridge holder 302 and of the housing or the ramp feature, which face each other. The angular clearance 336 may be greater than or equal to the angle of rotation during the second stage of movement. The cartridge holder 302 may have a ramp surface 329 as depicted or an interaction feature 334 as described previously.

The coding features, in particular the ones of the housing, i.e. the guide features 351, are axially offset from the ramp surfaces 353.

Figure 13:
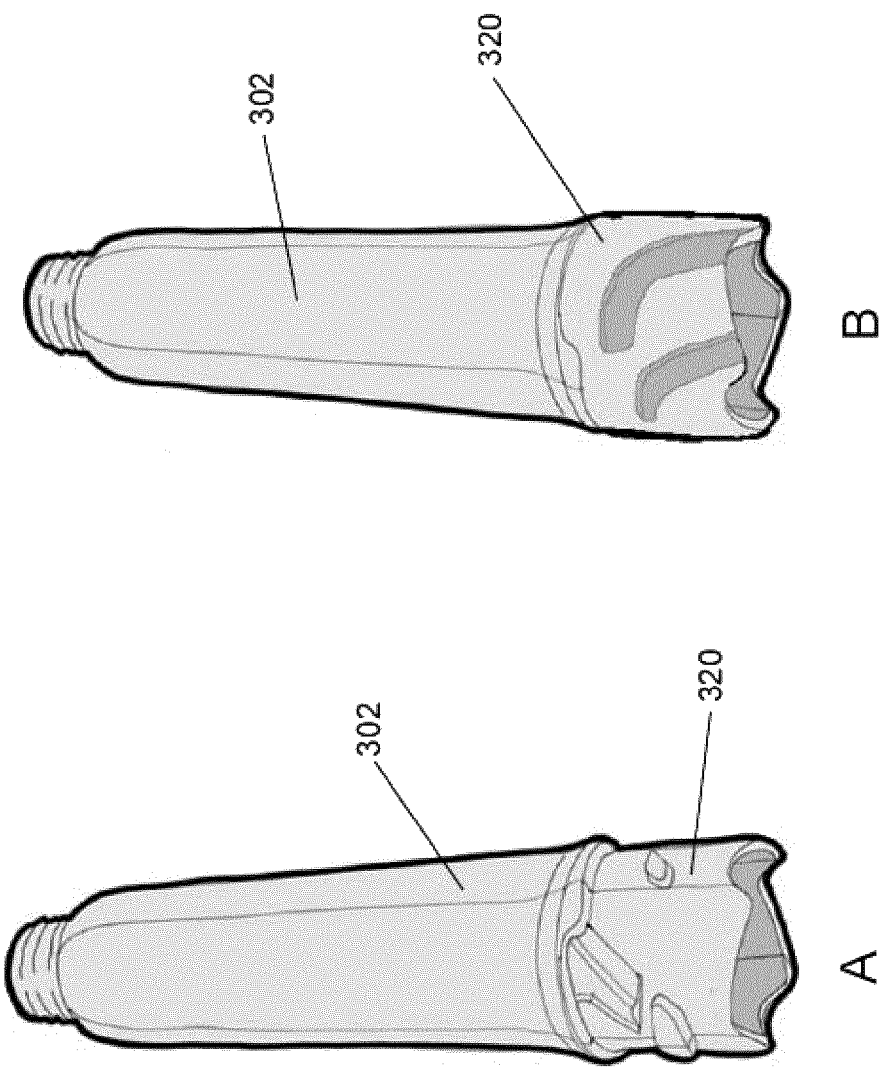

A further concept for creating a set of, e.g. two, non-compatible cartridge holders is illustrated in FIG. 13. In this embodiment, one of the Cartridge Holders (shown on the left hand of FIG. 13, representation A) has the bayonet lug features formed in the normal way on its outer cylindrical surface. The other holder (shown in the right hand image, representation B) has bayonet channels formed on its outer cylindrical surface; the lugs being formed for this variant on the inner wall of the associated housing.

It should be noted that this concept, i.e. interchanging the type of guide features—channels or tracks to lugs or vice versa—can be applied to any of the other embodiments as the general functionality of the interfaces formed by the guide features on the housing and the ones on the cartridge holder is not changed by switching lugs to channels and vice versa. This can be used for coding purposes but does not have to. Thus, when lug as guide features 327 are disclosed on the cartridge holder 302, they may, alternatively, be on the housing or housing part 350, and when the channels or tracks as guide features 351 are shown on the housing or housing part 350, they may, alternatively, be on the cartridge holder.

Figure 14:
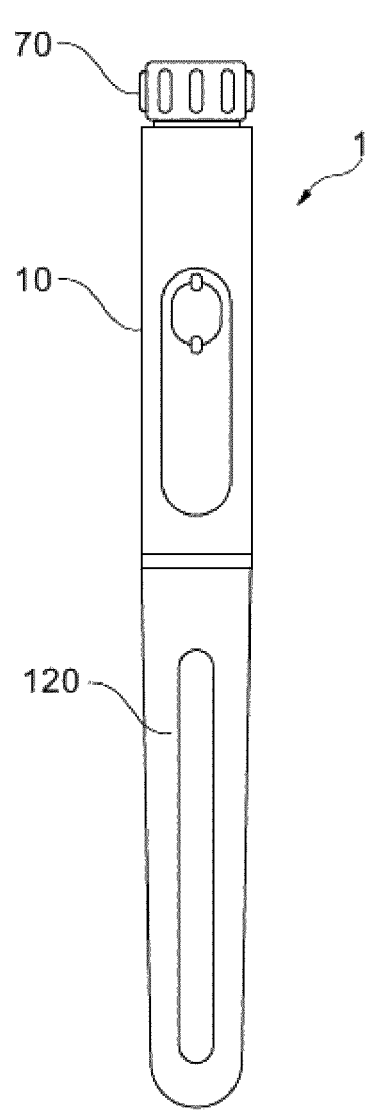
FIGS. 14 and 15 show an embodiment of a drug delivery device in two different situations.
Figure 15:
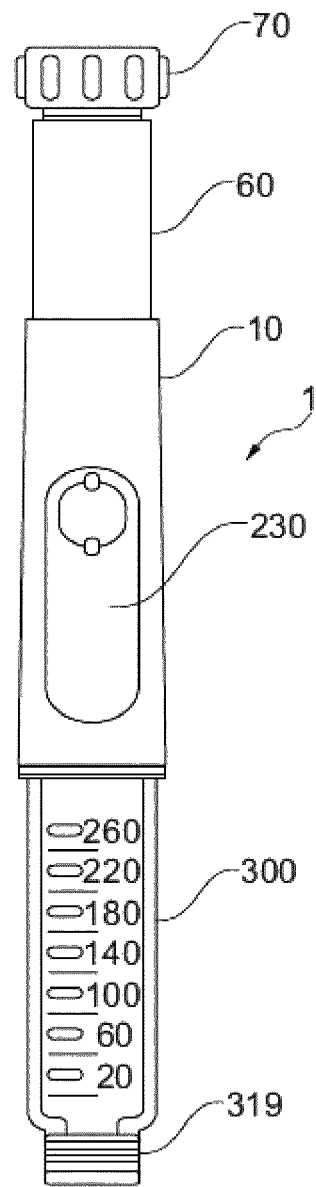

FIGS. 14 and 15 schematically illustrate embodiments of a drug delivery device suitable to be used in conjunction with the disclosed cartridge assemblies or systems and mechanisms. FIG. 14 shows the device 1 in a condition where a cap 120 is attached and covers the cartridge assembly 300 or unit. In FIG. 15 the cap has been removed. The cartridge assembly 300 is, expediently releasably, connected to a main body or housing 10 of the drug delivery device 1 as depicted in FIG. 6. The housing expediently defines the outer contour of the device and may be formed sleeve-like. The housing part 350 may be retained in the interior of housing 10. A needle unit can be connected to the needle connector 319 in order to dispense drug or medicament from the device 1. A dose setting member 70 is movably retained in the housing 10 and can be manipulated by the user to set a dose. For example, it can be rotated relative to the housing to set a dose. The device may be a variable dose device, where the size of the dose is not predetermined by the design of the drive mechanism retained in the housing but rather may be changed by the user. In FIG. 15, a dose set condition of the drug delivery device is illustrated, where the numeral depicted in window 230 is changed as compared to FIG. 14 such that it illustrates the size of the currently set dose. The device may be designed such that, during dose setting, the dose setting member 70 is displaced proximally relative to the housing 10. Alternatively, the dose setting member may stay in the same axial position independently of the set dose. From the position depicted in FIG. 15, a dispensing action may be initiated, expediently by moving or exerting a force in the distal direction onto the dose setting member 70 or a dose dispensing member provided in a proximal end section of the drug delivery device 1. To dispense the dose, the bung is displaced distally relative to the cartridge body 340, e.g. by a piston rod of the device (not explicitly shown).

By using the coding systems discussed above, it can be ensured that only that type of cartridge unit 300 including the specific drug or medicament, drug formulation or medicament formulation and/or volume, for which the drive mechanism in the housing 10 is designed can be connected to the housing 10.

The scope of protection is not limited to the examples given herein above. Any invention disclosed herein is embodied in each novel characteristic and each combination of characteristics, which particularly includes every combination of any features which are stated in the claims, even if this feature or this combination of features is not explicitly stated in the claims or in the examples.

REFERENCE NUMERALS 300 cartridge assembly
301 cartridge
302 cartridge holder
303 cartridge retaining section
304 inner wall
305 opening
306 dispensing end
307 drug
308 septum
309 septum retainer
310 head portion
311 main body portion
312 neck portion 313 cartridge surface
314 shoulder surface
315 distal end wall
316 opening
317 distal region
318 main body region
319 needle connector
320 connection region
321 step
322 fixing feature
323 injection gate mark
324 fixing surface
325 opening
326 surface
327 guide feature
328 securing feature
329 ramp surface
330 coding feature
331 shoulder region
332 surface
333 surface
334 ramp interaction feature
335 surface
336 angular clearance
340 cartridge body
341 reinforcement section
342 cartridge support feature
350 housing part
351 guide feature
351a,b section
352 distal end
353 ramp surface
1 drug delivery device
120 cap
70 dose setting member
10 housing
230 window
A thickness
B distance

The invention claimed is:

1. A system for a drug delivery device, the system comprising:
a housing; and
a cartridge unit that is attachable to the housing or releasably attached to the housing, wherein the cartridge unit comprises:
a cartridge unit guide feature, the cartridge unit guide feature being provided to establish a guiding interface with the housing in order to guide relative movement of the cartridge unit and the housing with respect to one another when attaching the cartridge unit to the housing, and wherein the cartridge unit comprises:
a cartridge unit interface feature, the cartridge unit interface feature being provided to form a further interface, in addition to the guiding interface, with the housing of the further interface being established when the cartridge unit is attached to the housing,
wherein the guiding interface is a bayonet-type interface which defines at least two different stages of movement between the cartridge unit and the housing when the cartridge unit is attached to the housing, a first stage with at least axial movement by a first stage axial distance in a first stage axial direction and a second stage with at least rotational movement by a second stage angle in a second stage rotational direction, and
wherein the further interface is or comprises a ramp interface; and
at least one cartridge unit coding structure, the cartridge unit coding structure being provided to establish a coding interface with at least one housing coding feature of a housing coding structure of the housing before the second stage of movement,
wherein the cartridge unit coding structure comprises one or more cartridge unit coding features, wherein the respective cartridge unit coding feature is an axially extending feature which is delimited in an angular direction by a surface which has an axial extension which is greater than or equal to the first stage axial distance.

2. The system of claim 1, wherein the system is configured such that the cartridge unit is moved relative to the housing in the second stage by a second stage axial distance in a second stage axial direction opposite to the first stage axial direction when the cartridge unit is attached to the housing, wherein the movement by the second stage axial distance is defined or governed by the ramp interface.

3. The system of claim 2, wherein the housing comprises a housing interface feature which is configured to interact with the cartridge unit interface feature to establish the further interface, wherein at least one of the housing interface feature and the cartridge unit interface feature comprises a ramp surface, and wherein a slope of the ramp surface is equal to a slope defined by the second stage axial distance and the second stage angle.

4. The system of claim 2, wherein the housing comprises a housing interface feature which is configured to interact with the cartridge unit interface feature to establish the further interface, wherein at least one of the housing interface feature and the cartridge unit interface feature comprises a ramp surface, and wherein the height difference between opposite ends of the ramp surface is greater than or equal to the second stage axial distance.

5. The system of claim 1, wherein the housing comprises a housing interface feature which is configured to interact with the cartridge unit interface feature to establish the further interface, wherein at least one of the housing interface feature and the cartridge unit interface feature comprises a ramp surface.

6. The system of claim 1, wherein the cartridge unit coding structure comprises one or more cartridge unit coding features, the respective cartridge unit coding feature being axially separated from the cartridge unit interface feature.

7. The system of claim 1, wherein the housing comprises a housing interface feature which is configured to interact with the cartridge unit interface feature to establish the further interface, wherein at least one of the housing interface feature and the cartridge unit interface feature comprises a ramp surface, and wherein the respective housing coding feature or the respective cartridge unit coding feature is formed by a feature which is part of the same ramp structure as the ramp surface but angularly offset from the ramp surface.

8. The system of claim 1, wherein the cartridge unit is a cartridge assembly which comprises a cartridge holder and a cartridge, the cartridge containing a drug, wherein the cartridge is permanently secured in the cartridge holder.

9. A set of drug delivery devices comprising the arrangement of claim 8, wherein the housing is a first housing of a first drug delivery device and the arrangement comprises a second housing of a second drug delivery device, where the second cartridge unit can be attached to the second housing and the first cartridge unit cannot on account of the different cartridge unit coding structures, and wherein the second cartridge unit and the second housing have cartridge unit interface features and housing interface features which cooperate to form a further interface, in addition to a guiding interface, the further interface comprising a ramp interface, wherein a first ramp surface which governs the ramp interface between the first housing and the first cartridge unit and a second ramp surface which governs the ramp interface between the second housing and the second cartridge unit have the same slope.

10. The set of drug delivery devices of claim 9, wherein the first ramp surface is part of a first ramp structure which comprises a plurality of ramp surfaces and the second ramp surface is part of a second ramp structure which comprises a plurality of ramp surfaces, wherein the first ramp structure and the second ramp structure are configured alike.

11. An arrangement comprising:
a system for a drug delivery device, the system comprising:
  a housing; and
  a cartridge unit that is attachable to the housing or releasably attached to the housing, wherein the cartridge unit comprises:
    a cartridge unit guide feature, the cartridge unit guide feature being provided to establish a guiding interface with the housing in order to guide relative movement of the cartridge unit and the housing with respect to one another when attaching the cartridge unit to the housing, and wherein the cartridge unit comprises:
      a cartridge unit interface feature, the cartridge unit interface feature being provided to form a further interface, in addition to the guiding interface, with the housing of the further interface being established when the cartridge unit is attached to the housing,
    wherein the guiding interface is a bayonet-type interface which defines at least two different stages of movement between the cartridge unit and the housing when the cartridge unit is attached to the housing, a first stage with at least axial movement by a first stage axial distance in a first stage axial direction and a second stage with at least rotational movement by a second stage angle in a second stage rotational direction, and wherein the further interface is or comprises a ramp interface,
wherein the cartridge unit of the system for the drug delivery device is a first cartridge unit and the arrangement comprises a second cartridge unit, the second cartridge unit having a second cartridge unit guide feature and a second cartridge unit interface feature,
wherein the first cartridge unit and the second cartridge unit contain different drugs or drug formulations and/or comprise cartridges of different dimensions,
wherein cartridge unit coding structures of the first and second cartridge unit are different, such that a cartridge unit coding structure of the first cartridge unit and a housing coding structure match one another such that the first cartridge unit can be attached to the housing and a cartridge unit coding structure of the second cartridge unit and the housing coding structure do not match one another, such that the second cartridge unit cannot be attached to the housing,
wherein at least one of the cartridge unit coding structures is provided to establish a coding interface with at least one housing coding feature of the housing coding structure of the housing before the second stage of movement, and
wherein the at least one cartridge unit coding structure comprises one or more cartridge unit coding features, wherein the respective cartridge unit coding feature is an axially extending feature which is delimited in an angular direction by a surface which has an axial extension which is greater than or equal to the first stage axial distance.

12. The arrangement of claim 11, wherein the housing is a first housing and the arrangement comprises a second housing, where the second cartridge unit can be attached to the second housing and the first cartridge unit cannot on account of the different cartridge unit coding structures, and wherein the second cartridge unit and the second housing have cartridge unit interface features and housing interface features which cooperate to form a further interface, in addition to a guiding interface, the further interface comprising a ramp interface, wherein a first ramp surface which governs the ramp interface between the first housing and the first cartridge unit and a second ramp surface which governs the ramp interface between the second housing and the second cartridge unit have the same slope.

13. The arrangement of claim 12, wherein the first ramp surface is part of a first ramp structure which comprises a plurality of ramp surfaces and the second ramp surface is part of a second ramp structure which comprises a plurality of ramp surfaces, wherein the first ramp structure and the second ramp structure are configured alike.

14. A drug delivery device comprising:
a medicament; and
a system comprising:
  a housing; and
  a cartridge unit that contains the medicament and is attachable to the housing or releasably attached to the housing, wherein the cartridge unit comprises:
    a cartridge unit guide feature, the cartridge unit guide feature being provided to establish a guiding interface with the housing in order to guide relative movement of the cartridge unit and the housing with respect to one another when attaching the cartridge unit to the housing, and wherein the cartridge unit comprises:
      a cartridge unit interface feature, the cartridge unit interface feature being provided to form a further interface, in addition to the guiding interface, with the housing of the further interface being established when the cartridge unit is attached to the housing,
    wherein the guiding interface is a bayonet-type interface which defines at least two different stages of movement between the cartridge unit and the housing when the cartridge unit is attached to the housing, a first stage with at least axial movement by a first stage axial distance in a first stage axial direction and a second stage with at least rotational movement by a second stage angle in a second stage rotational direction, and
    wherein the further interface is or comprises a ramp interface, and at least one cartridge unit coding structure, the cartridge unit coding structure being provided to establish a coding interface with at least one housing coding feature of a housing coding structure of the housing before the second stage of movement, wherein the cartridge unit coding structure comprises one or more cartridge unit coding features, wherein the respective cartridge unit coding feature is an axially extending feature which is delimited in an angular direction by a surface which has an axial extension which is greater than or equal to the first stage axial distance.

15. The drug delivery device of claim 14, wherein the system is configured such that the cartridge unit is moved relative to the housing in the second stage by a second stage axial distance in a second stage axial direction opposite to the first stage axial direction when the cartridge unit is attached to the housing, wherein the movement by the second stage axial distance is defined or governed by the ramp interface.

16. The drug delivery device of claim 15, wherein the housing comprises a housing interface feature which is configured to interact with the cartridge unit interface feature to establish the further interface, wherein at least one of the housing interface feature and the cartridge unit interface feature comprises a ramp surface, and wherein a slope of the ramp surface is equal to a slope defined by the second stage axial distance and the second stage angle.

17. The drug delivery device of claim 15, wherein the housing comprises a housing interface feature which is configured to interact with the cartridge unit interface feature to establish the further interface, wherein at least one of the housing interface feature and the cartridge unit interface feature comprises a ramp surface, and wherein the height difference between opposite ends of the ramp surface is greater than or equal to the second stage axial distance.

18. The drug delivery device of claim 14, wherein the housing comprises a housing interface feature which is configured to interact with the cartridge unit interface feature to establish the further interface, wherein at least one of the housing interface feature and the cartridge unit interface feature comprises a ramp surface.

* * * * *